United States Patent [19]
Kuijpers et al.

[11] Patent Number: 5,733,523
[45] Date of Patent: Mar. 31, 1998

[54] TARGETED DELIVERY OF A THERAPEUTIC ENTITY USING COMPLEMENTARY OLIGONUCLEOTIDES

[75] Inventors: Wilhelmus H. A. Kuijpers, Eindhoven; Franciscus M. Kaspersen, Hoesch; Constant A. A. van Boeckel, Oss, all of Netherlands

[73] Assignee: Akzo Nobel N.V., Arnhem, Netherlands

[21] Appl. No.: 378,327

[22] Filed: Jan. 26, 1995

Related U.S. Application Data

[60] Division of Ser. No. 990,968, Dec. 15, 1992, abandoned, which is a continuation-in-part of Ser. No. 805,398, Dec. 10, 1991, abandoned.

[30] Foreign Application Priority Data

Dec. 10, 1990 [NL] Netherlands ............ 90-02714

[51] Int. Cl.$^6$ .......... A61K 51/10; A61K 39/44; C07K 16/00; C07K 17/00
[52] U.S. Cl. .......... 424/1.73; 424/178.1; 530/391.1; 530/391.3; 530/391.9
[58] Field of Search .......... 424/1.73, 178.1; 530/391.1, 391.7, 391.9; 536/22.1

[56] References Cited

U.S. PATENT DOCUMENTS

| | | | |
|---|---|---|---|
| 4,863,713 | 9/1989 | Goodwin et al. | 424/9 |
| 5,045,451 | 9/1991 | Uhr et al. | 435/7.23 |

FOREIGN PATENT DOCUMENTS

| | | |
|---|---|---|
| 8805077 | 7/1988 | WIPO. |
| 89 05853 | 6/1989 | WIPO. |
| 89 06702 | 7/1989 | WIPO. |
| 89 12110 | 12/1989 | WIPO. |
| 90 10448 | 9/1990 | WIPO. |
| 90 12802 | 11/1990 | WIPO. |

OTHER PUBLICATIONS

Chemical Reviews, vol. 90, No. 4, Jun. 1990, American Chemical Society, E. Uhlmann et al., "Antisense Oligonucleotides: A New Therapeutic Principle".
Chemical Abstracts, vol. 112, No. 11, Mar., 1990, No. 95109K (Columbus, Ohio, US).
J.A. Fidanza et al., "Introduction of Reporter Groups at Specific Sites in DNA Containing Phosphorothioate Diesters," J.Am.Chem.Soc., 111, 1989, pp. 9117–9119.
Martindale, The Extra Pharmacopoeia, Ed. James Reynolds, 1989, p. 1380.
Canevari et al., Ann Oncol., vol. 5/8, pp. 698–901 (1994).
Hermentin, Behring Inst. Mitt, No. 82, pp. 197–215 (1988).

Primary Examiner—Ponnathapura Achutamurthy
Attorney, Agent, or Firm—Mary E. Gormley

[57] ABSTRACT

The invention relates to novel labelled modified oligonucleotides useful for anti-sense therapy, a conjugate of a targeting moiety, such as an antibody and a modified oligonucleotide complementary to the labelled oligonucleotide, the combination of both being useful in therapy of viral infections, tumours and (auto)immunodiseases. Also disclosed are pharmaceutical formulations comprising the various compounds.

7 Claims, 6 Drawing Sheets

TARGETED DELIVERY OF A THERAPEUTIC ENTITY USING COMPLEMENTARY OLIGONUCLEOTIDES

This application is a division of U.S. Ser. No. 07/990,968, filed Dec. 15, 1992, abandoned, which is a continuation-in-part of U.S. Ser. No. 07/805,398, filed Dec. 10, 1991, abandoned

FIELD OF THE INVENTION

The invention relates to modified oligonucleotides which are radioactively labelled and to conjugates containing modified oligonucleotides. The invention further relates to pharmaceutical compositions containing the same, and methods of treatment using said compositions.

BACKGROUND OF THE INVENTION

Radioactively labelled oligonucleotides are known, for instance as probes used in hybridization assays. The use of such oligonucleotides in vivo generally will not be possible, because unmodified DNA and RNA are quickly metabolized in vivo. For in vivo purposes modified oligonucleotides have been described in E. Uhlmann and A. Peyman: Chemical Reviews, 90, 543 (1990).

In so-called "anti-sense oligonucleotide" therapy, synthetic, modified DNA or RNA fragments, which may or may not be conjugated with enzymes or cytostatics, are directed towards complementary nucleic acid sequences (DNA or RNA) which are present in the "target" cells, for example of tumors or cells infected by a virus. Modification of the anti-sense oligonucleotide is necessary for the desired stability in circulation (inter alia, they must be able to withstand endogenous enzymes) and, in addition, the penetration in cells and tissues can be improved as a result of the modification. The anti-sense oligonucleotide is complementary to a nucleic acid sequence in the target cell and may inhibit DNA transcription, mRNA translation, or (viral) nucleic acid replication.

Up to now "anti-sense oligonucleotides" have not been conjugated with chemical groups which are labelled with radioactive isotopes which can be used in radioimmunotherapy.

SUMMARY OF THE INVENTION

The present invention relates to modified "anti-sense oligonucleotides" which are labelled with isotopes which can be used therapeutically (radioactive anti-sense nucleotide: RAN) and the use of RANs in anti-cancer and anti-viral therapy. Moreover, the RANs can be labelled in such a way that the localization of the complementary nucleic acid (fragment) is taken into account. If the RAN has to have an intracellular action, isotopes which emit Auger electrons are preferred (such as $^{77}Br$, $^{80}Br$, $^{125}I$, $^{123}I$, and $^{201}Tl$), while in the case of extracellular localization alpha- or beta-emitting isotopes (such as $^{105}Rh$, $^{177}Lu$, $^{199}Au$, $^{109}Pd$, $^{77}As$, $^{142}Pr$, $^{149}Pm$, $^{159}Gd$, $^{166}Ho$, and preferably $^{67}Cu$, $^{90}Y$, $^{131}I$, $^{153}Sm$, $^{186}Re$, $^{211}At$, $^{212}Pb$, $^{212}Bi$, $^{213}Bi$, $^{225}Bi$ isotopes) are preferred. The latter category of isotopes is also preferred if the RAN has to reach its "target" both inside and outside the cell. Also non-radio isotopes like $^{10}B$, $^{57}Fe$, and $^{127}I$, which can be transferred into therapeutic isotopes by external radiation, for example by X-ray or neutron radiation, are suitable. Radioisotopes having only signalling utility, like some radioisotopes of phosphorous, iodine, hydrogen, carbon, cobalt, nickel, and the like, are not encompassed in the definition of the isotopes of this invention, which can be used therapeutically.

BRIEF DESCRIPTION OF THE DRAWINGS

FIG. 4B is a graph showing that during incubation with the RAN it hybridizes specifically with the antibody conjugated oligonucleotides.

DETAILED DESCRIPTION OF THE INVENTION

Figure 1B:
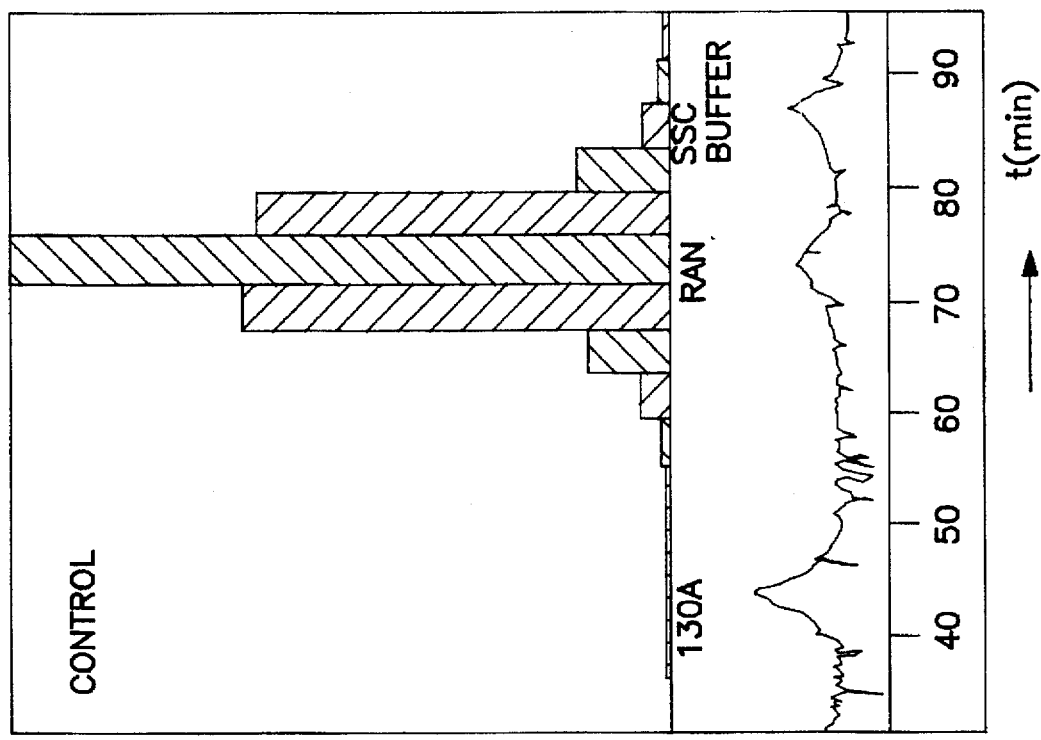
FIG. 1B is a control elution.

The RANs may be prepared according to any known technique for synthesis of oligonucleotides, for example as described in E. Uhlmann and A. Peyman: Chemical Reviews, 90, 543 (1990). Natural sugar backbones (ribose and deoxyribose) or their enantiomers may be chosen, possibly suitably modified, for instance 2'-O-methyl ribose, but it will also be possible to use stereoisomers (enantiomers α instead of β nucleosides) to choose other backbones such as deoxyglucose, as long as they can be made more resistant to endogenous enzymes and as long as they can provide for base pairing of the oligonucleotides, with a sufficient Tm (melting temperature). Also the phosphate binding between the sugars may be replaced by a more stable bond (in vivo), such as —$CH_2$—$SO_2$—$CH_2$—, or —O—$CH_2$—O—. The RANs may be either linear oligonucleotides or circular oligonucleotides. The bases may be the natural bases (A,U,C,G,T,), but they may also be rare bases such as xanthine, hypoxanthine and the nucleosides iso-guanosine and iso-cytidine described in Benner et al., J. Am. Chem. Soc.,111, 21, 1989.

Preferred RANs are radioactively labelled, modified oligonucleotides of type I.

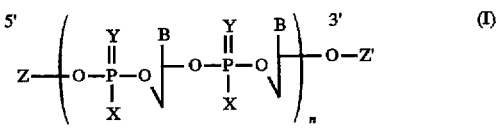

n=5–20,

B=nucleoside base (C, G, A, T, U) or analogous base,

X=$O^-$, $S^-$, N-dialkyl, O-alkyl, alkyl and/or combinations thereof,

Y=O and/or S,

Z is H, alkyl, aralkyl, acyl, nucleoside, or a chemical group which contains an isotope with therapeutic activity, and Z' has the same meaning as Z or is a chemical group which is suitable for conjugation with a targeting moiety and which contains a reactive aldehyde, maleimide, bromoacetyl, $NH_2$, or SH group, provided that Z' is not H or nucleoside when X is O⁻ or Y is O, and that one but not both of Z and Z' is the chemical group containing the isotope.

In this definition alkyl means an alkyl group having 1–6 carbon atoms, like methyl, ethyl, propyl, sec-butyl, pentyl, and hexyl. Preferred alkyl groups have 1–4 carbon atoms and most preferred is the methyl group.

Aralkyl is an aralkyl group the alkyl moiety of which is the alkyl group as defined previously, and the aryl moiety is preferably a phenyl group, which may optionally be substituted by alkyl (as previously defined), alkoxy (O-alkyl, the alkyl as previously defined), OH, or halogen (F, Cl, Br, I).

Acyl means an acyl group derived from an aliphatic carboxylic acid having 1–12 carbon atoms, like formic acid, acetic acid, propionic acid, and dodecylcarboxylic acid. Preferred acyl groups have 1–6 carbon atoms, and most preferred is the acetyl group.

The chemical group used in the definition of Z and Z' can be any chemical group suitable for carrying a radioisotope. Suitable groups whether or not bound to a linker moiety (see e.g. P. S. Nelson et al., Nucleic acid Research, 17 (1989), 7179 and 7187), are for example ethylenediaminetetraacetic acid (EDTA), diethylenetriaminepentaacetic acid ((DTPA), poly-azamacrocycles, benzyl-DTPA, benzyl-EDTA, LiLo, IDAC and other activated derivatives of polyaminopolycarboxylates, some antibiotics, crown ethers, other macrocyclic compounds, natural chelating proteins such as trans-ferrin, apoferritin and metallothionein and diazotized aromatic amines, chelators of the NxSy-type (x+y=4), such as $MAG_3$ (especially for Re isotopes), and for halogen isotopes also p—HO—$C_6H_4$—$(CH_2)_n$, n being 2 or more, known from the literature, for example from C. F. Meares et al., Br. J. Cancer, 62 (1990) Suppl. X, 21–26; M. Studer et al., Bioconjugate Chem., 3 (1992), 337, and R. Subramanian et al., ibid., 3 (1992), 248.

The base sequence is determined by the base sequence of the "target nucleic acid fragment", the RAN being complementary to the sequence of the latter (for instance C–G and A–T as complementary bases).

Another aspect of the invention provides a conjugate of a targeting moiety such as an antibody or a fragment or a derivative thereof, directed to an antigen associated with a target cell and a modified oligonucleotide which is complementary to a RAN. It is also possible to choose any other member of a specific binding pair which complementary member is associated with a specific group of target cells as a targeting moiety, such as ligands for receptors and the like. The conjugate can be administered to a subject; it will localize at the target site and after allowing sufficient time for said localization a RAN is administered, which will be bound by the complementary modified oligonucleotide in the conjugate. This will greatly enhance the possibilities of targeted therapy as used in for instance the combat of (auto) immune diseases, viral infections and tumors. Such a pre-targeting program is shown in scheme 1.

Scheme 1A:

Therapeutic application of radiolabelled antisense nucleotides (RANs).

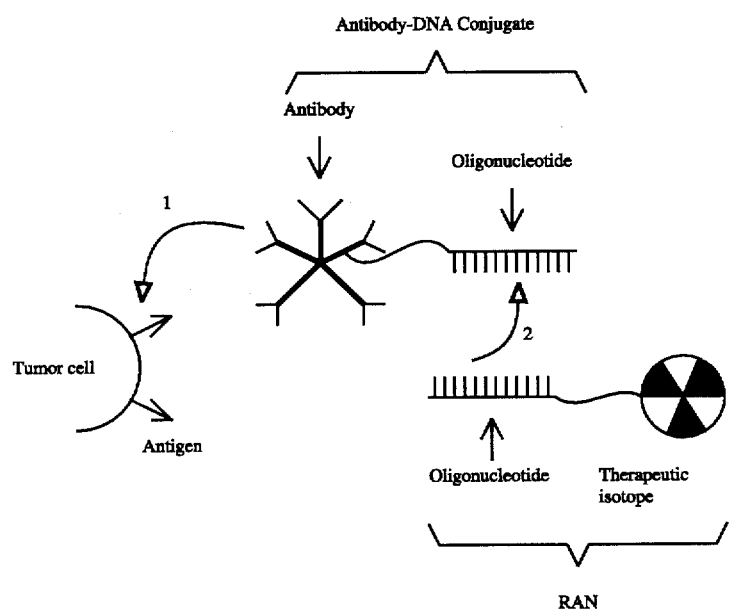

Scheme 1B:
Therapeutic application of radiolabelled antisense nucleotides (RANs).

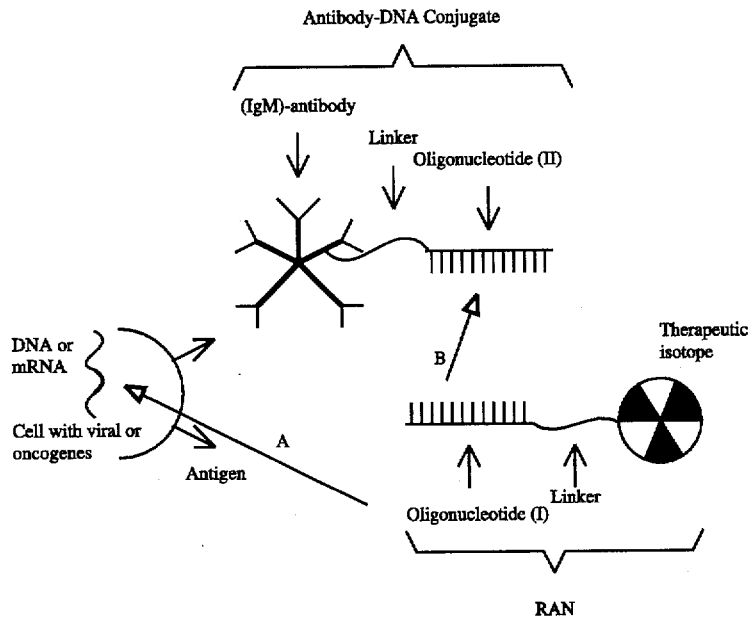

The use of specific antibodies in tumor therapy is known. However, the use of radioactively labelled antibodies is restricted by the slow uptake in the "target" tissues, as a result of which there is an unfavorable ratio of exposure to radiation between diseased and healthy tissues.

A so-called "pre-targeting program" is used in order to improve this unfavorable ratio. In this program non-radioactive bi-functional targeting moieties such as antibody conjugates are dispatched to the diseased tissues (initial binding) and subsequently, at the time when the antibodies are distributed in an optimum ratio between diseased and healthy tissues, a radioactively labelled ligand is administered which is distributed rapidly over the tissues and adheres to the second binding site of the antibody. However, possibilities for pre-targeting which are mentioned in the literature still have their limitations, inter alia as a result of, on the one hand, the low affinity of the second specific binding and, on the other hand, due to the use of substances foreign to the body, such as avidin (see Goodwin et al., J. Nucl. Med. 28, 722 (1987) and 29, 226 (1988)). The use of RANs has the advantage that RANs i) have a structure occurring naturally in the body, ii) enter into strong, specific bindings, iii) distribute rapidly and well over tissues and iv) the residence time in the human body can be optimized by means of the nature of the chemical modification.

If RANs are directed towards oligonucleotides bound to targeting moieties such as antibodies, the bound oligonucleotide must be complementary to the RAN and of type II:

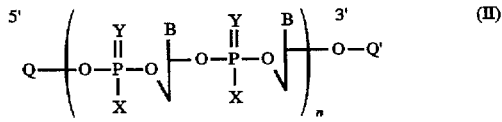

in which:
n=5–20.
B=nucleoside base.
X=O⁻, S⁻, N-dialkyl, O-alkyl, alkyl and/or combinations thereof.

Y=O and/or S.
one or both of Q and Q' is a chemical group which is suitable for conjugation with a targeting moiety and which contains a reactive aldehyde, maleimide, bromoacetyl, $NH_2$, or SH group, and the other Q or Q', if present, is H, alkyl, aralkyl, acyl or nucleoside.

Such groups (Q,Q') and conjugation techniques which are needed to couple Q or Q' to targeting moiety are described in the review article by J. Goodchild: Bioconjugate Chemistry 1, pages 165 to 187 inclusive (1990), which is incorporated by reference. Many more chemical groups are, however, suitable, and in practice the exact nature of such group is of no relevance for the invention as such. A person of ordinary skill can select a group that suits the best for a specific problem. Other groups and methods to link these to oligonucleotides and target moieties are, for instance, described by inter alia S. Cheng at al., Nucleic Acid Res., 11 (1990), 659; P. S. Nelson et al., Nucleic acid Research, 17 (1989), 7179 and 7187; A. Chollet, Nucleosides and Nucleotides, 9 (1990), 957; J. Czichos et al., Nucleic Acid Res., 17 (1989) 1563; B. C. F. Chu and L. E. Orgel, Nucleic Acid Res., 16 (1988), 3671; S. Nakagami et al., Biochem., 198 (1991), 75; and B. W. Baer et al. PCT patent application WO 91/04753. Optionally the type II nucleotide may be labelled with an isotype for imaging dosimetry.

It is preferred to couple several (type II) oligonucleotides to the targeting moiety, in order to increase the number of binding sites for the oligonucleotide of type I. An additional therapeutic effect is achieved if the oligonucleotide sequence corresponds to a sequence which is unique for an intracellular oncogene or viral gene derived nucleotide sequence (RNA or DNA).

RANs are prepared by labelling chemically synthesized, modified oligonucleotides (type I) with the desired radioactive isotope. The synthesis of modified nucleotides which are suitable both for the RAN (type I) and for type II is effected in accordance with known methods such as described in Chemical Reviews 90 pages 543 to 584 inclusive (1990), modifications such as methylphosphonates, phosphorus amidates, phosphorus thioates and alkylphosphotriesters being preferred, which preferably are incorporated in combination with naturally occurring phosphodiester bonds.

Because the last mentioned oligonucleotides are usually prepared with the aid of so-called "solid phase" synthesis, the groups to be labelled are preferably positioned at the 5' end. Examples of these groups in the case of labelling with radioactive halogens are:

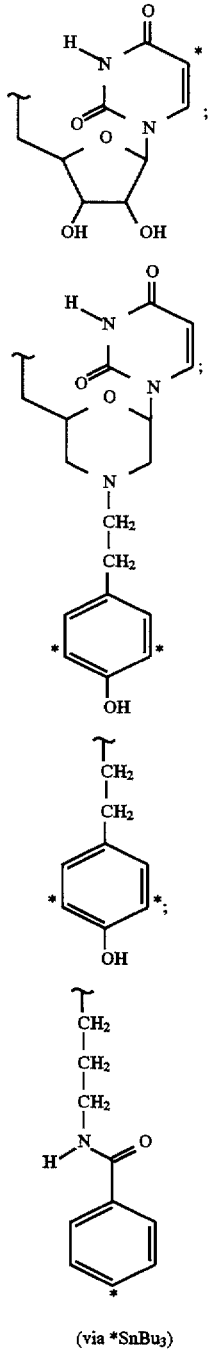

(via *SnBu₃)

where * is the site to which the radioactive halogen is attached. An alternative is direct halogenation of the nucleic acid bases. If radioactive metals are used, Z and/or Z' is a complex of a radioactive metal and a chelator such as DTPA macrocyclic chelating agents, $N_xS_x$ chelating agents and similar substances, such as:

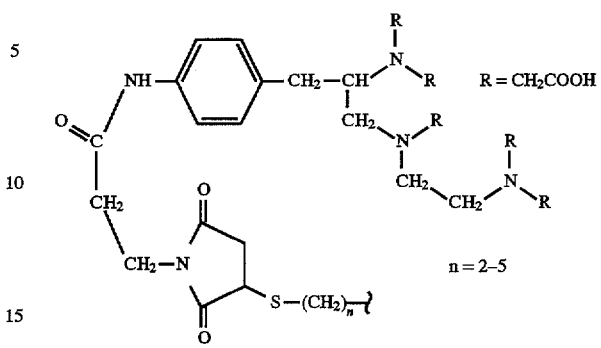

The RANs of the invention may be administered parenterally, and for humans preferably in a daily dosage of 0.001–1 mg per kg body weight, and the conjugate may be administered parenterally, and for humans preferably in a daily dosage of 0.01–100 mg per kg body weight. Mixed with pharmaceutically suitable auxiliaries and pharmaceutically suitable liquids, e.g. as described in the standard reference, Gennaro et al., Remington's Pharmaceutical Sciences, (18th ed., Mack Publishing Company, 1990, see especially Part 8: Pharmaceutical Preparations and Their Manufacture) the compounds may be processed to an injection preparation in the form of a solution.

For making dosage units the use of conventional additives is contemplated. In general any pharmaceutically acceptable additive which does not interfere with the function of the active compounds can be used. Stabilizers, for example scavengers for radiolysis, can also be added.

The invention further comprises a kit of parts for the elimination of specific cell populations. Such kit of parts comprises one or more dosage units containing a composition comprising a modified oligonucleotide labelled with a therapeutically active radio-isotope (preferably the oligonucleotide of type I), and one or more dosage units containing a composition comprising a conjugate of an antibody or a fragment or a derivative thereof and a modified oligonucleotide (preferably of type II). The oligonucleotide moiety of the active ingredient of the first composition is complementary to the oligonucleotide moiety of the active ingredient (the nucleotide) of the second composition.

A method of treating viral infections, tumors and (auto) immunodiseases by sequentially administering the oligonucleotides of the invention to patients is also an objective of the invention. A conjugate comprising a modified oligonucleotide, preferably the conjugate of type II is then administered in a therapeutically effective dosage, followed by administering a therapeutically effective dosage of an oligonucleotide comprising a therapeutically active radio-isotope, preferably the oligonucleotide of type I (RAN), of which the oligonucleotide moiety is complementary to the oligonucleotide moiety of the conjugate. The time between the administration of both components can vary from a few hours to 20 days. Preferably the second component is administered when the first component is bound by the target cell, which process can often be followed, for example when the conjugate is labelled with a diagnostic isotope (e.g. a gamma-emitter), by monitoring the patient. Sometimes it is necessary to repeat the first treatment with the conjugate to effect complete saturation. In individual cases the time schedule can be adapted in order to obtain a maximum effect.

The invention is further illustrated by the following examples.

EXPERIMENTAL

In antisense therapy, various DNA modifications have been introduced, mainly to enhance the stability of the oligonucleotide against nucleases and to improve the cellular uptake. Most commonly used are backbone-modified DNA analogues such as phosphorothioate, methylphosphonate and alkyl phosphotriester oligonucleotides. In all these cases, however, introduction of modified phosphate groups should not lead to poorer solubility of the oligonucleotide in water or to a decrease of the stability of the complex with the target sequence.

As mentioned, both DNA fragments, the RAN and the fragment conjugated to the targeting moiety, have to be modified to protect them against nuclease degradation. The main nuclease activity in the blood origins from 3'-exonucleases. Therefore, modification of the phosphodiester(s) at the 3'-end of the oligonucleotide has shown to be important. As the oligonucleotide bound to the targeting moiety should be stable for quite a long period (2–3 days), this fragment should be more severely modified than the RAN, but not to an extent that the material becomes immunogenic.

Three sets of type I/II oligonucleotides have been prepared: A, B, and C respectively. Experiments performed with these sets of oligonucleotides are described in the corresponding sections A–C.

Section A

A-I: U5'-5' Gp(Me)CCGGCGCAAGCGp(Me)C 3' [SEQ ID NO:1]
A-II: U5'-5' Gp(Me)CGCTp(Me)TGCGp(Me)CCGp(Me)Gp(Me)C 3' [SEQ ID NO:2]
p (Me) denotes a methylphosphonate Methylphosphonate linkages can be easily introduced into DNA fragments using standard (phosphoramidite) DNA chemistry. Furthermore, this modification is stable towards the chemical conditions necessary for conjugation and radiolabelling and the introduction of neutral internucleoside linkages diminishes the non-specific binding of the highly charged oligonucleotides to positively charged blood proteins.

Using an Applied Biosystems DNA synthesizer (model 381A), the complementary DNA fragments A-I and A-II, bearing 2 and 5 methylphosphonate linkages respectively, were synthesized (obtained after deprotection using ammonia in methanol during 3 days and purification with the aid of gel permeation chromatography). Duplex stability.

The stability of a duplex between two complementary DNA strands is expressed as the melting temperature Tm. This temperature, at which half of the helical structure is lost, can be monitored by measuring the absorbance at 260 nm as a function of temperature. The Tm-value for the DNA duplex between A-I and A-II in 0.1M NaCl, 0.01M Tris.HCl (pH 7.0) was found to be 57° C. Under physiological conditions in vivo (37° C.) an efficient hybridization will occur.

At the 5'-end of the modified DNA fragments (A-I and A-II) a 5'—5' linked uridine nucleotide was introduced. This uridine moiety offers, after oxidation of the cis diol, the possibility to incorporate various amino-containing linkers via reductive amination (Scheme 2).

Obviously the highest modified DNA fragment A-II was used for conjugation with the antibody.

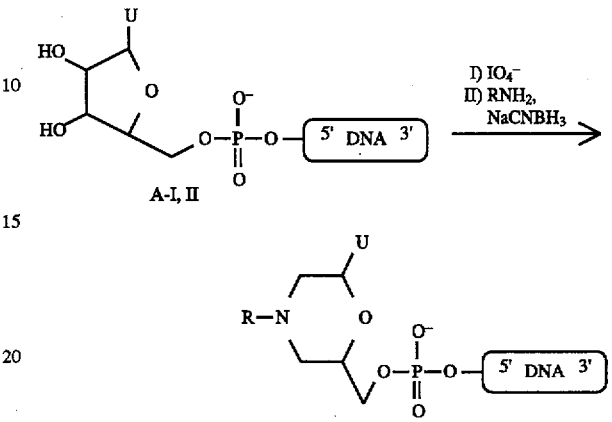

Scheme 2: Incorporation of amino-containing linkers via 5'—5' linked uridine.

Example A-1
Preparation of radiolabelled oligonucleotides (RANs).

A RAN was obtained by radioactive labelling of the synthetic nucleotide (A-I).
U 5'-5'-Gp(Me)CCGGCGCAAGCGp(Me)C 3' [SEQ ID NO:3]

By reacting the oligonucleotide with sodium periodate (0.05M; 30 eq.) in sodium acetate buffer (0.1M, pH=4.75) during 1 hour at 0° C. in the dark, the ribose (of U) was converted to a dialdehyde. After removing the excess periodate on a SEPHADEX G-10 column, the dialdehyde was aminated in a solution of 0.05 M tyramine in 0.1M phosphate buffer (pH 6.9)/methanol (2:1 v/v).

After 30 minutes at room temperature sodium cyanoborohydride (0.1M; 30 eq.) in methanol was added. The reduction was allowed to proceed overnight at room temperature, after which an additional amount (30 eq.) of sodium cyanoborohydride was added (1 hour, room temperature). The reaction mixture was concentrated and applied to a SEPHADEX G-25 column using 0.05M TEAB as eluent. DNA-containing fractions were collected and lyophilized to yield the derivatized oligonucleotide A-III.

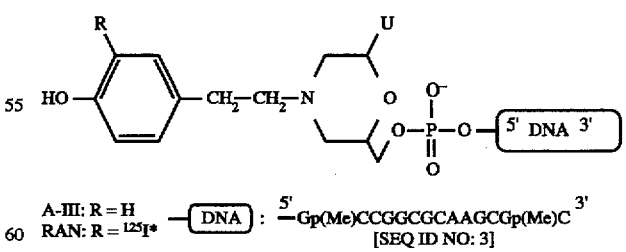

A-III: R = H
RAN: R = $^{125}$I*

Scheme 3.

The p-hydroxyphenylethyl moiety of oligonucleotide A-III could be easily labelled with Na$^{125}$I in the presence of iodogen$^R$. Briefly, an Eppendorf reaction tube was coated with iodogen$^R$ (50 µg) by drying an iodogen $^R$ solution in methylene chloride by means of nitrogen. To the reaction tube was added 10 μg Na$^{125}$I solution (≈2 mCi). The iodination was allowed to proceed for 15 minutes at room temperature with occasional shaking. The RAN was purified on SEPHADEX PD10 using either PBS buffer or 2×SSC buffer (for hybridization studies). The specific activity of the RAN thus obtained was 35 μCi/μg.

Example A-2
Preparation of antibody-oligonucleotide conjugates.

First, oligonucleotide A-II was derivatized with an activated thiol linker in an analogous way as described for the derivatization of oligonucleotide. Briefly, oligonucleotide A-II was oxidized with 0.05M sodium periodate (12.5 eq.) in 0.12M sodium acetate buffer (pH=4.75) during 1 hour at 0° C. in the dark. Subsequent to removal of excess periodate (SEPHADEX G-10) the dialdehyde was aminated with 0.04M S-pyridylcysteamine. HCl (30 eq.) in 0.1M phosphate buffer(pH 8.0)/methanol (2:1 v/v), followed by reduction with sodium cyanoborohydride (5 eq.) in methanol during 16 hours at room temperature. An additional amount of sodium cyanoborohydride (5 eq.) was added before purification of the oligonucleotide on a SEPHADEX G-25 column using 0.05M TEAB as eluent. Lyophilization of the DNA containing fractions afforded oligonucleotide A-IV containing a thiol linker activated as a 2-pyridyldisulfide. According to UV-absorbance of the pyridine-thione released upon reduction of the disulfide, approximately 45% of the oligonucleotide contained the activated thiol linker.

A-IV:

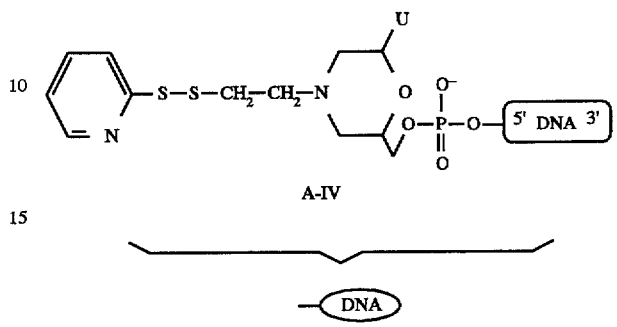

Scheme 4

As disulfide linked protein-DNA conjugates may be insufficiently stable in in vivo systems, the maleimide coupling strategy can be advantageous. Generally, in this approach the antibody is derivatized with maleimide groups by treatment of the protein with succinimidyl-4-(N-maleimidomethyl) cyclohexane-1-carboxylate (SMCC).

Subsequently, a conjugate with the thiol-containing oligonucleotide is formed via a stable thioether linkage (Scheme 5).

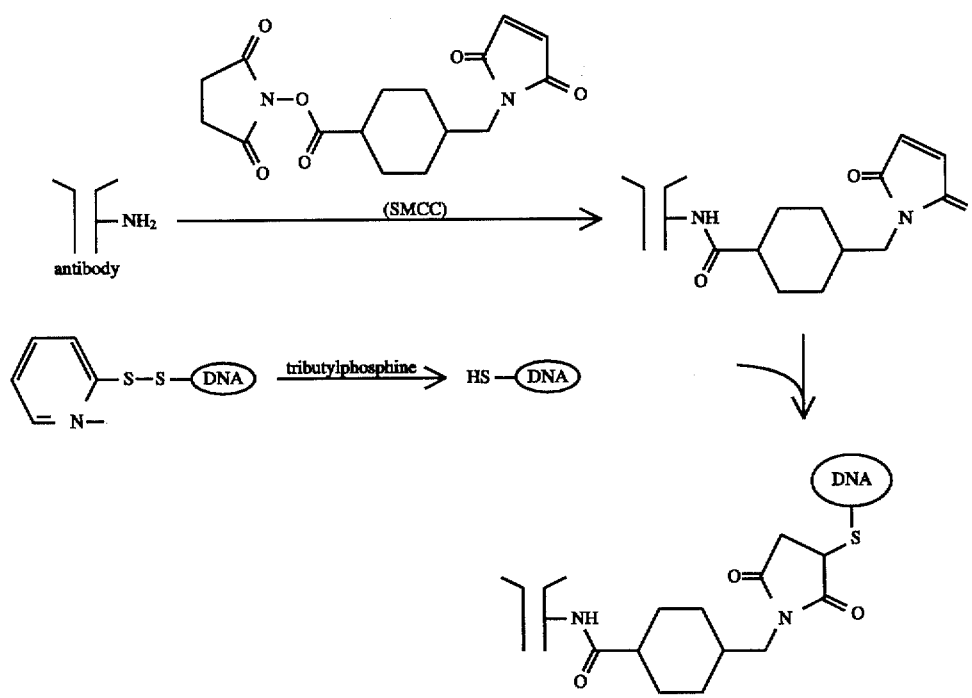

Scheme 5: Preparation of antibody-oligonucleotide conjugates.

Example A-3

In vitro experiments with the anti-HCG antibody 130A.

Initially, the anti-HCG antibody 130A was used to investigate the proper conditions for conjugation of the oligonucleotide.

Conjugate preparation.

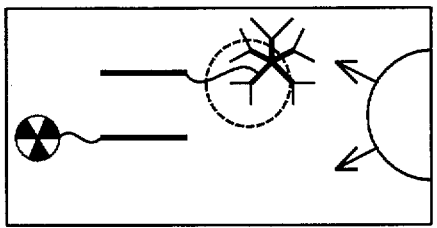

First, the IgG 130A in 0.05M phosphate buffer (pH 7.5) was reacted with SMCC (0.01 in DMF) during 1 hour at room temperature in the dark. An average of 10 maleimide groups per antibody was introduced upon treatment with 60 eq. of SMCC. The antibody was purified on a PD-10 column using 0.05M phosphate/0.1M NaCl/5 MM EDTA (pH 6.0) as eluent. After reduction of the 2-pyridyldisulfide activated oligonucleotide in 0.1M phosphate buffer (pH 8.0)/methanol (2:1 v/v) was effected by treatment with tributylphosphine (1 eq., 5 min, r.t.), the thiol containing DNA fragment (50 eq. with respect to the antibody) was reacted immediately with the maleimide-derivatized antibody (Scheme 5). The conjugation was allowed to proceed overnight at 4° C., followed by blocking of the unreacted maleimide groups with cysteamine.

The presence of covalently attached oligonucleotides in the conjugate preparation could be demonstrated by Iso-Electric Focussing (IEF) and SDS-PAGE. In IEF a shift of the isoelectric point towards lower pH-value was observed, and SDS-PAGE showed an increase in molecular size in comparison with unconjugated IgG 130A.

The antibody-oligonucleotide conjugate could easily be separated from excess of unreacted oligonucleotide by gel filtration on SEPHACRYL S-100. HR column run at 4° C. with PBS as eluent. The fractions containing antibody-conjugate were stored at 4° C.

Based on the 260 nm/280 nm absorbance ratio of the purified conjugate a 3:1 molar composition of oligonucleotide and antibody was determined.

Hybridization studies.

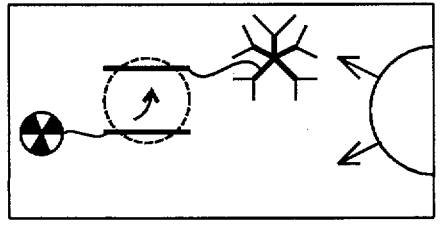

Figure 1A:
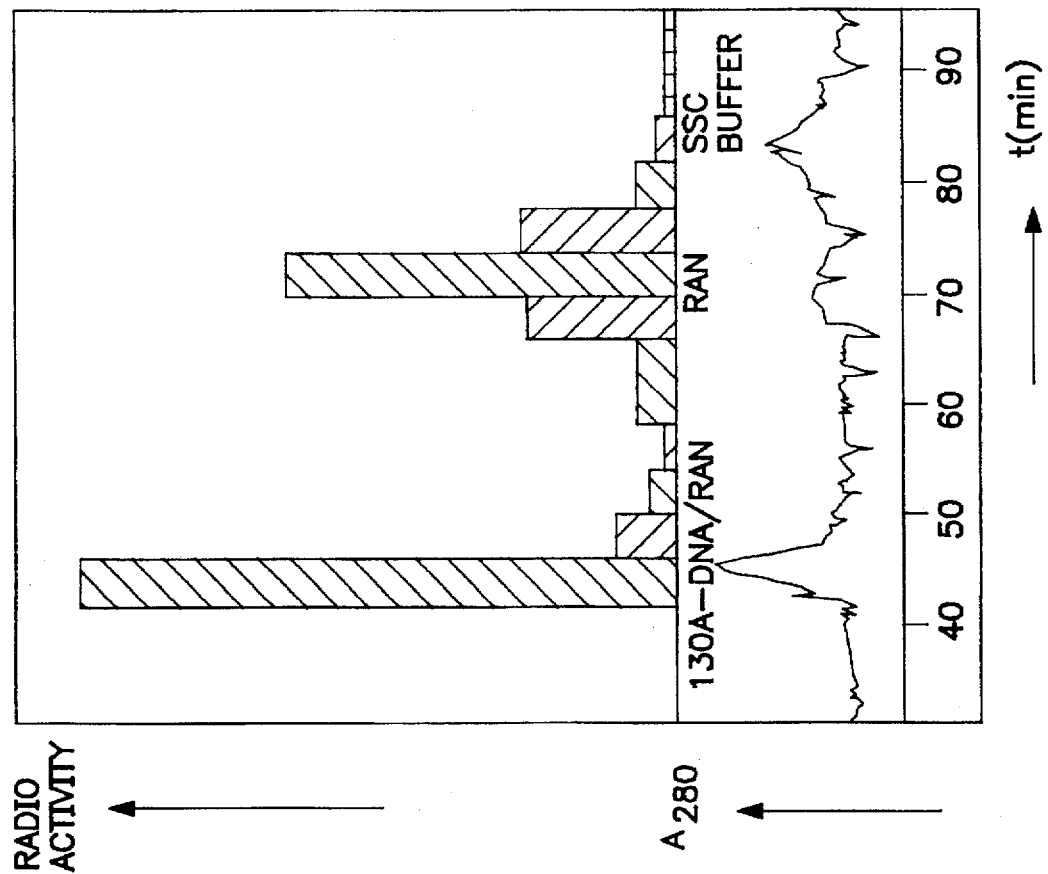
FIG. 1A shows the absorbance at 280 nm and the radioactivity of the eluted fractions of the gel filtration of the IgG130A-DNA/RAN hybridization mixture

The RAN was allowed to hybridize with the oligonucleotides of the antibody conjugate (10 µg/ml) in 2×SSC buffer. A slight excess (approx. 1.2 eq.) of RAN was used in comparison with the total amount of conjugated DNA fragments. After 1 hr hybridization at room temperature, the mixture was applied on a SEPHACRYL S-100 column and eluted with PBS buffer at 4° C. in order to separate unhybridized RAN from the conjugate/RAN complex. The absorbance at 280 nm and the radioactivity of the eluted fractions were measured (FIG. 1A). FIG. 1A shows the gel filtration of IgG130A-DNA/RAN hybridization mixture.

The elution profile showed radioactivity in both the conjugate peak and RAN peak. Approximately 45% of the eluted radioactivity was present in the peak containing the antibody-conjugate. In order to exclude non-specific binding of the RAN to the antibody, a control experiment was carried out in which underivatized IgG 130A was incubated with the RAN in the hybridization buffer. Gel filtration of the mixture revealed that less than 0.1% of the registered radioactivity was present in the antibody fraction.

These experiments demonstrate that the RAN is indeed capable to recognize the complementary sequence on the antibody via a specific hybridization mechanism.

Antigen binding studies.

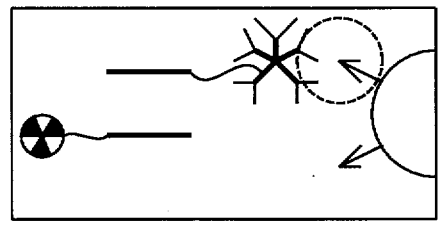

Part of the hybridization mixture (see above) was incubated with HCG-coated SEPHAROSE beads, to see whether the antibody-oligonucleotide conjugate had retained its antigen binding properties.

After 90 minutes at room temperature, the mixture was centrifuged and the supernatant was removed. The beads were washed several times with hybridization buffer before the remaining radioactivity on the beads was determined. A 150-f old higher radioactivity was measured relative to the control experiment, in which HCG-SEPHAROSE beads were incubated with a mixture of the RAN and IgG 130A and treated as above. This illustrates that no non-specific binding of the RAN to the antibody (or beads) occurs.

In conclusion, these antigen binding studies clearly indicate that the antibody after conjugation with the oligonucleotide has retained its ability to bind specifically to antigens in vitro.

Example A-4

In vitro experiments with the human anti-tumor antibody 16-88.

IgM 16-88 was activated with maleimide groups by treatment with SMCC as described for the 130A antibody. Since an IgM offers more reactive sites than an IgG, a slighter excess of SMCC was used in comparison with IgG 130A derivatization.

Reaction with 17 eq. of SMCC afforded an average derivatization with 8.5 maleimide groups, as was determined spectrophotometrically. The activated antibody was reacted immediately with freshly reduced (tributylphosphine) oligonucleotide A-IV (40 eq. with respect to the antibody). After conjugation overnight (4° C.) and subsequent blocking of unreacted maleimide groups with cysteamine, the antibody-oligonucleotide conjugate was separated from excess oligonucleotide and other reagents on a SEPHACRYL S-100 HR column with PBS buffer as eluent at 4° C. Although a shift in the 260 nm/280 nm absorbance ratio was observed for the purified conjugate (0.63) in comparison with IgM 16-88 (0.57), a precise quantification of the number of conjugated oligonucleotides was not possible, due to the dominating UV-absorbance of the protein. Based on our experience with the 130A antibody, however, we estimate that 2-3 oligonucleotides are linked to the antibody.

In analogy with the IgG 130A experiments, the IgM 16-88-DNA conjugate was incubated with the RAN (approx. 2 eq. with respect to the conjugate) in 2×SSC buffer to allow hybridization of the complementary DNA fragments. After a hybridization period of 1 hr. at room temperature, a S-100 column (PBS buffer, 4° C.) was used to separate the antibody containing fraction from unhybridized RAN. Determination of radioactivity in both fractions revealed that 16% of the eluted counts was present in the antibody-conjugate fraction. As with IgG 130A, the control experiment, in which RAN and IgM 16-88 were incubated and subsequently separated, showed that negligible non-specific binding of RAN to IgM 16-88 had occurred: 0.2% of eluted radioactivity was present in the antibody peak.

These findings were confirmed by a series of dot-blot hybridization experiments. In this assay a dilution series of the IgM 16-88-DNA conjugate was immobilized on a nitrocellulose filter. After blocking the filter with BLOTTO to suppress non-specific binding, it was incubated with RAN during 2 hr. at room temperature in 2×SSC buffer. Then, the filter was washed and imaged with autoradiography, showing a good dilution pattern.

In a parallel experiment, a similar dilution series of IgM 16-88-DNA conjugate was treated with an equal amount of RAN diluted 100-fold with unlabelled oligonucleotide A-III. The radioactivity spotted in this series perfectly matched the pattern for 100-fold dilution in the first experiment. In the control experiment, in which a nitrocellulose filter immobilized with IgM 16-88 was incubated with RAN, only background radioactivity was detected.

Summarizing, these results prove that despite of the huge dimensions of the IgM antibody the RAN is still capable to interact specifically with the conjugated oligonucleotides.

Antigen binding studies.

The antigen binding capacity of the IgM 16-88-DNA conjugate was, as with the IgG 130A conjugate, examined by incubation of SEPHAROSE beads coated with CTA-1, the cognate antigen of IgM 16-88, with a hybridization mixture of conjugate and RAN. In comparison with the control IgM 16-88/RAN mixture 17.5-fold radioactivity on the CTA-coated beads was measured.

Apart from the above experiment, in which the RAN was hybridized with the conjugate before the latter had bound to the antigen, an additional test was carried out mimicking the pre-targeting "binding sequence". Thus, first CTA-coated beads were incubated with IgM 16-88-DNA conjugate overnight at 4° C. (step 1). After removal of excess conjugate and several washings, the beads were incubated with RAN during 2½hr. at room temperature in 2×SSC buffer (step 2). Likewise, a competition experiment was performed including hybridization with the same amount of RAN, diluted 100-fold with unlabelled oligonucleotide A-III. Subsequent to removal of the supernatant and several washings, the remaining radioactivity on the beads was determined. The results of these experiments are summarized in Table 1.

TABLE 1

| Step 1 | Step 2 | Relative Radioactivity |
|---|---|---|
| IgM 16-88-DNA | RAN | 10.6 |
| IgM 16-88 (control) | RAN | 1.8 |
| IgM 16-88-DNA | RAN/DNA(A-III) (1:100) | 1.4 |
| IgM 16-88 (control) | RAN/DNA(A-III) (1:100) | 1 |

As expected, the highest radioactivity is found for the pre-targeting experiment with undiluted RAN. Moreover, the data clearly demonstrate the competitive behavior of the unlabelled oligonucleotides.

Above experiments (with CTA-coated beads acting as a model for antigen expressing tumor cells) illustrate that a radiolabelled oligonucleotide is able to recognize its complementary sequence on an antibody-conjugate, even when the latter is bound to its antigen. In this manner, pre-targeting based on DNA hybridization has been shown to be successful in vitro.

Human antitumor antibody 16-88 and its antigen are disclosed in U.S. Pat. No. 5,338,832, which is enclosed by reference. The 16-88-producing cell line is deposited at the ATCC, Rockville, Md., USA, under accession no. HB 8495.

Section B

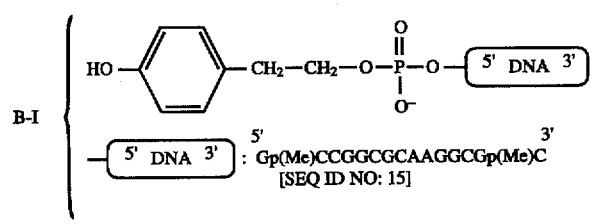

-continued
Section B

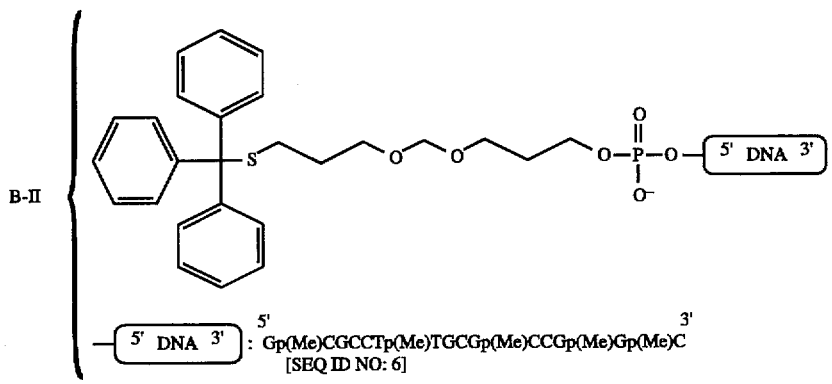

p(Me) denotes a methylphosphate

Section A reported studies on DNA—DNA pretargeting that were performed with automatically synthesized chimeric phosphodiester/methylphosphonate oligonucleotides containing a 5'—5' linked uridine moiety for further derivatization. Although good results were obtained as far as DNA conjugation and radiolabeling are concerned, derivatization according to the "uridine" procedure is quite laborious. Moreover, it is difficult to control the various reaction steps performed on the oligonucleotides with respect to propagation of the reaction and occurrence of side-reactions. Only in case of the pyridyldisulfide functionalized oligonucleotides prepared for conjugation purposes, quantitative analysis of the final degree of derivatization was possible. Thus, UV-monitoring of released pyridinethione after reduction of the disulfide linkage showed that approximately 45% of the oligonucleotide contained the thiopyridyl-protected thiol linker.

It hardly needs to be stressed that incorporation of linkers during solid-phase oligonucleotide assembly is a far more ideal approach than functionalization afterwards. Side-reactions are minimized since all reactive functionalities, e.g of the nucleobases, are protected during solid-phase synthesis. Moreover, additional purifications of the derivatized oligonucleotides are no longer required, since, after deprotection and work-up, the oligonucleotide is purified with the linker group already attached.

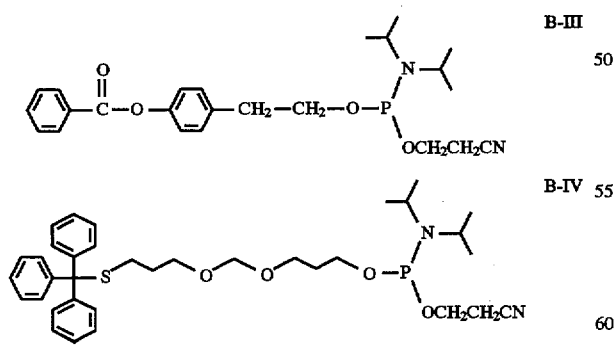

Scheme 6.

Effective radiolabeling of oligonucleotides with iodine isotopes ($^{125}$I, $^{131}$I) can be accomplished when tyrosine-like functionalities are introduced. Phosphoramidite B-III was used for the direct introduction of a p-hydroxyphenylethyl function at the 5'-end of a DNA fragment during solid-phase synthesis. The phenolic hydroxyl group of the commercially available p-hydroxyphenethyl alcohol was protected first with a benzoyl group before phosphitylation of the aliphatic hydroxyl function following a standard procedure. This afforded compound B-III which was used in the solid-phase synthesis of oligonucleotide B-I according to the conventional phosphoramidite approach. The methylphosphonate linkages in this 15-mer were introduced by applying appropriately base-protected methylphosphonamidites. After coupling of phosphoramidite B-III in the last synthetic cycle, the fully protected oligonucleotide was treated with ammonia/methanol in order to deprotect the phosphate-and base-amino functions as well as the phenolic hydroxyl group at the 5'-end. Purification by gel filtration chromatography afforded the partially methylphosphonate modified oligonucleotide B-I, the homogeneity of which was established by HPLC analysis (MonoQ).

One of the approaches for introducing a 5'-terminal thiol on oligonucleotides involves the use of an alkyl spacer bearing a trityl protected thiol at one end and a phosphoramidite at the other.

Since for the pretargeting studies a longer spacer than in the commercially available reagents would be favorable, phosphoramidite B-IV was prepared. Instead of a long alkyl chain a spacer was prepared which contains some oxygen atoms in order to ensure both solubility of the amidite during coupling conditions and sufficient hydrophilicity of the completely deprotected oligonucleotide. The synthetic route to compound B-IV commences with the preparation of the methylthiomethyl ether of mono-benzoylated 1,3-propanediol using methylsulfide in the presence of benzoylperoxide. Condensation of the methylthiomethylene derivative with 3-bromopropanol was accomplished with N-iodosuccinimide and catalytic tri-fluoromethanesulphonic acid as the promoter. The terminal bromo-group of the resulting spacer was converted into a trityl-protected thiol function using tritylmercaptane sodium salt. Finally, saponification of the benzoyl ether afforded a free hydroxyl group which was phosphitylated according to a standard procedure. Phosphoramidite B-IV was applied for the solid-phase synthesis of the partially methylphosphonate oligonucleotide B-II.

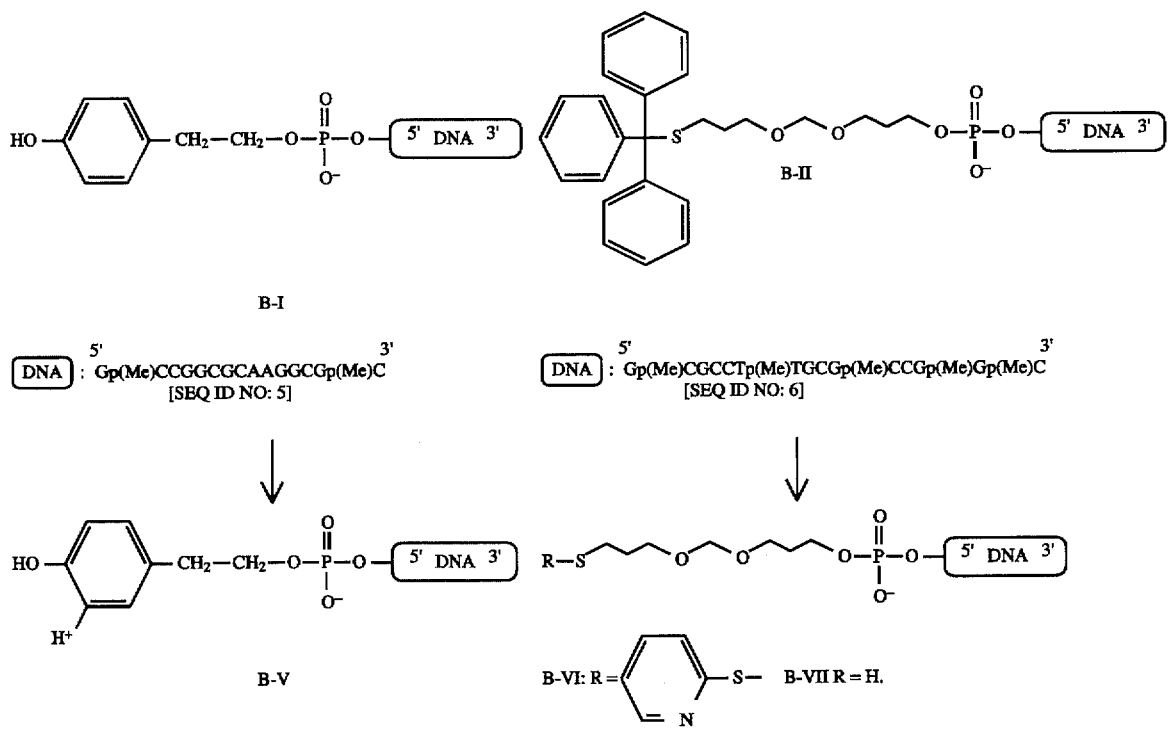

Scheme 7

Scheme 7.

Treatment of oligonucleotide B-II (SCHEME 7) with silver nitrate to remove the trityl protective group and subsequent addition of DTE (dithioerythritol), yielded the free thiol containing DNA fragment B-VII (SCHEME 7) which was separated from the resulting salts by gel filtration in the presence of a small amount of DTE to prevent the formation of disulfide. Oligonucleotide B-VII was treated with excess of dithiodipyridine to give the thiopyridyl protected fragment B-VI (SCHEME 7), which after purification can be used in the conjugation procedure. UV monitoring of the release of pyridinethione upon reduction of oligonucleotide B-VI revealed that 65% of the total amount of DNA contained the pyridyldisulfide group.

Example B-1

Preparation of radiolabelled oligonucleotides (RANs)

Radioiodination of oligonucleotide B-I in the presence of Iodogen$^R$ could be accomplished with similar labeling efficiencies as in previously described studies The RAN B-V thus obtained was used in the in vitro pretargeting assay described in Example B-3.

A solution of oligonucleotide B-I (SCHEME 7) in phosphate buffered saline (PBS) (200 µl; 0.65 mg/ml) was transferred to an iodogen-coated (125 µg) polypropylene tube and incubated for 30 min at 4° C. with $^{131}$Na (400 µCi). The RAN was purified on a SEPHADEX G-25 (PD-10, Pharmacia) using PBS as eluent. DNA-containing fractions were pooled (1.25 ml) and total radioactivity (100 µCi) was measured. The solution was diluted with M505/10% FCS (0.25 ml) (fetal calf serum) to give a final solution of approx. 80 ng of RAN B-V (SCHEME 7) with a specific activity of 0.85 µCi/µg.

Example B-2

Preparation of antibody-oligonucleotide conjugates.

The antibody oligonucleotide conjugates were obtained via the maleimide coupling strategy (as in SCHEME 5). To a solution of oligonucleotide 5 (SCHEME 7) (0.25 µmol) in water (200 µl) was added 1.0M silver nitrate solution in water (25 µl). The reaction mixture, which turned slightly pale, was incubated for 2 hours at room temperature in the dark and was occasionally vortexed. In order to liberate the free thiol containing oligonucleotide, excess of 0.5M dithioerythritol (DTE) in water (70 µl) was added, which caused precipitation of the silver salt of DTE. After an incubation period of 2 hours at room temperature with occasional vortex mixing, the reaction mixture was applied to a SEPHADEX G-25 column (1 cm×65 cm), equilibrated and eluted with 0.1M phosphate buffer (pH 5.5), containing 1 mM EDTA and 1 mM DTE. The appropriate fractions, checked by MonoQ-HPLC analysis, were pooled and concentrated in vacuo to a volume of approximately 2 ml. To this solution was added dithiodipyridine (DTDP) (27.5 mg, 125 µmol) and sufficient acetonitrile to make DTDP completely dissolve. A small amount of potassium hydroxide solution in water (1.0M) was added to give a final pH of 8.0. The reaction mixture was incubated overnight at room temperature. Acetonitrile was evaporated under reduced pressure and the remaining suspension was washed thoroughly with diethyl ether(3×2 ml) to remove excess DTDP. The aqueous layer was neutralized by the addition of acetic acid (10% v/v) and concentrated in vacuo to a small volume (approx. 0.5 ml). The derivatized DNA was purified by gel filtration on a SEPHADEX G-25 column (1 cm×65 cm), using 0.05M TEAA (pH 5.5) as eluent. DNA-containing fractions, as monitored by MonoQ-HPLC analysis, were pooled and lyophilized twice.

Anti-CEA antibody SC 20 (1.1 mg; 7 nmol) in 50 mM phosphate buffer (pH 7.5) (2.0 ml) was incubated with 0.05M SMCC in dimethylformamide (7 µl; 50 eq.) for 2 hours at room temperature in the dark. Gel filtration on SEPHADEX G-25 (PD-10 column, Pharmacia) was performed in order to remove excess SMCC. The column was equilibrated and eluted with 50 mM phosphate buffer (pH 6.0), containing 0.1M NaCl and 5 mM EDTA. Presence of antibody in the eluted fractions was checked by measuring UV-absorbance at 280 nm. Antibody containing fractions were pooled (total volume 3.0 ml) to give a final concentration of 0.35 mg anti-CEA/ml (1 mg/ml=1.4 absorbance units).

In order to determine the substitution ratio, a small amount of this solution (500 µl) was reacted with 50 mM cysteamine in phosphate buffer (pH 6.0) (200 µl) during 10 minutes, followed by back-titration of unreacted cysteamine with 0.01M 5, 5'-dithiobis-(2-nitrobenzoic acid) (DTNB) in 0.1M phosphate buffer (pH 8.0) (33 µl). The amount of maleimide groups present can be quantified spectrophotometrically by measuring absorbance at 412 nm ($\epsilon$=13,600$M^{-1}.cm^{-1}$) relative to DTNB reduction with cysteamine in the absence of maleimide. In this way, an average loading of 6.8 maleimide groups per anti-CEA was found.

Oligonucleotide B-VI (Scheme 7) (73 nmol) was dissolved in 0.1M phosphate buffer (pH 8.0)/methanol (2:1 v/v) (375 µl). A stream of nitrogen was bubbled through to deoxygenize the DNA solution. Reduction of the pyridyl disulfide group was accomplished by the addition of 5 mM tributylphosphine solution in degassed isopropanol (15 µl, 75 nmol). The reaction mixture was incubated for 15 minutes at room temperature before the addition of maleimide-derivatized anti-CEA in degassed phosphate buffer (pH 6.0) (915 µl 10.35 mg/ml; 2 nmol anti-CEA). Conjugation was allowed to proceed overnight at 4° C. Finally, cysteamine (5 mM in water, 5 µl) was added to block unreacted maleimide groups. The anti-CEA-DNA conjugate was purified on a SEPHACRYL S-100 HR column (1.6×60 cm), using PBS as eluent. Fractions containing the immunoconjugate were pooled and concentrated to a final volume of 600 µl by ultrafiltration on Amicon YM10. A final antibody concentration of 0.27 mg/ml was found by measuring $A_{280}$.

The number of oligonucleotides conjugated per antibody was determined as described before. Following extinction coefficients for pure DNA and anti-CEA were used to derive a relation between the measured $A_{260}/A_{280}$ ratio and the conjugation ratio: $\epsilon_{anti-CEA,280}$=2.24×10$^5$$M^{-1}.cm^{-1}$; $\epsilon_{DNA, 260}$=1.26×10$^5$$M^{-1}.cm^{-1}$. The $A_{260}/A_{280}$ ratio for the anti-CEA-DNA conjugate was found to be 1.06, corresponding with an average conjugation ratio of 2.8 oligonucleotides per antibody.

Example B-3
In vitro pretargeting assay

The human tumor cell line LS174T has been widely applied in several antibody targeting studies. LS174T is a colon adenocarcinoma cell line expressing the carcino-embryonic antigen (CEA). The LS174T cell system has shown to be a valuable tool to study uptake kinetics and toxicity of radiolabeled antibodies for immunotherapy purposes. Such experiments have been performed both in vitro using monolayer cultures or multicell spheroids (>500 µm diameter) and in vivo with LS174T xenografts in nude mice. In the study described here LS174T cell clusters of approximately 5 cells in diameter (microemboli) were used. Whereas saturation of cells with antibody can take several days, the binding of MoAb to microemboli should reach completion within hours.

Figure 2A:
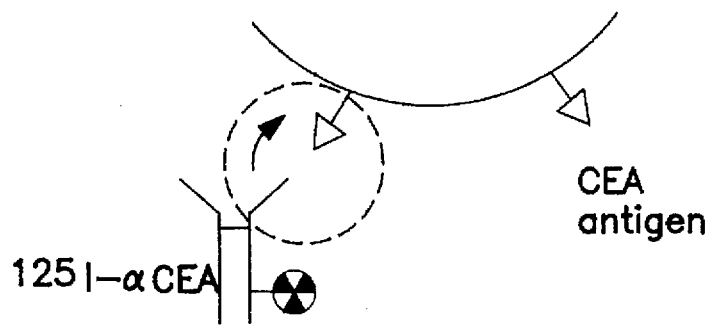
FIG. 2A shows a graphic representation the in vivo pre-targeting of $^{125}I$-anti-CEA monoclonal to tumor cells and FIG. 2B is a graph showing the amount bound to the surface of cells and internalized over time.
Figure 2B:
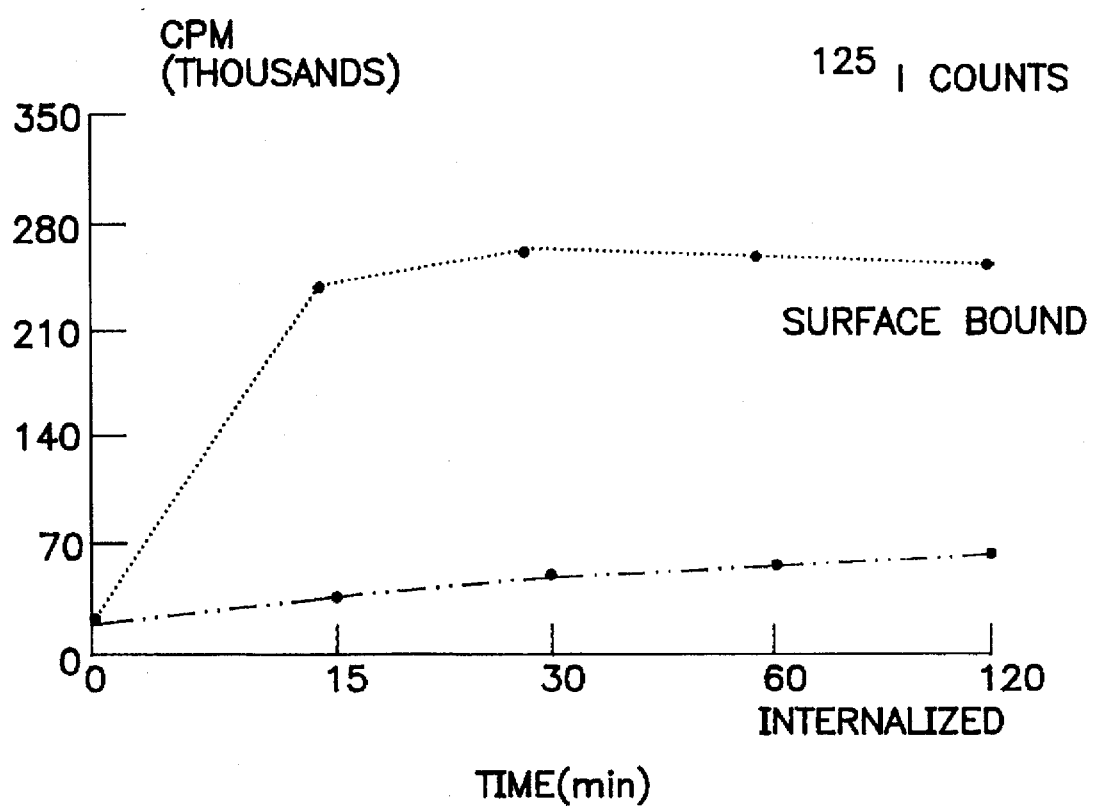

Screening of the binding properties of several monoclonal antibodies in LS174T cell systems showed the monoclonal antibody SC 20, directed against the carcino-embryonic antigen (CEA), to be an ideal candidate for pretargeting investigations. Targeting of $^{125}$I-labeled anti-CEA MoAb to LS174T microemboli revealed a rapid localization of the antibody at the tumor cells, which reaches saturation within 30 minutes (FIG. 2B). Moreover, determination of remaining radioactivity in the microemboli after stripping of the cell surface revealed that only a negligible fraction of the antibody is internalized in the cells.

For the in vitro studies described here the anti-CEA-DNA conjugate was labelled with $^{125}$I in a standard Iodogen$^R$ labeling procedure:

Anti-CEA-DNA conjugate (160 µg) in PBS buffer (600 µl) was radioiodinated with the iodogen technique. Thus, the conjugate solution was added to an iodogen-coated (90 µg) polypropylene tube and incubated with 200 µCi of Na$^{125}$I during 30 minutes at 4° C. with occasional vortex-mixing. Excess radioiodide was removed by gel filtration on SEPHADEX G-25 (PD-10, Pharmacia) using PBS as eluent.

Immunoconjugate-containing fractions were pooled (1.5 ml) and total radioactivity was determined (37 µCi). The PBS solution was diluted with M505/10% FCS (0.25 ml) to give a final conjugate concentration of approx. 80 ng/µl with a specific activity of 0.25 µCi/µg.

In the same manner, for the control series, pure anti-CEA antibody was radiolabeled with $^{125}$I. Thus, anti-CEA (150 µg) was incubated with 200 µCi $^{125}$I and after 30 minutes at 4° C. purified on SEPHADEX G-25 (PD-10, Pharmacia). Radioactivity in the pooled antibody fractions (1.0 ml) was measured(63 µCi) and M505/10% FCS (0.5 ml) was added. The final solution contained approx. 90 ng antibody/µl with a specific activity of 0.45 µCi/µg.

LS174T microemboli in M505/10% FCS medium (50 µl; 4.10$^7$ cells/ml) were transferred into Eppendorf tubes and kept on ice. The suspension was incubated with $^{125}$I-labeled anti-CEA-DNA conjugate (50 µl, 1.0 µCi) for 30 minutes at 37° C. The samples were cooled on ice and centrifuged lightly to pellet the cells. The supernatant was removed by suction and the cells were extensively washed with ice-cold medium (3 times). The cell pellets were resuspended in fresh medium (50 µl) before the addition of $^{131}$I-RAN B-V (SCHEME 7) (10 µl, 0.7 µCi). Incubations of RAN were carried out in triplicate at 37° C. for 30, 60 and 120 minutes respectively. At the end of the incubation period, samples were cooled on ice and centrifuged. The supernatant was removed and the cell pellets were thoroughly washed with ice-cold medium (three times). Finally, the remaining radioactivity (both $^{125}$I and $^{131}$I) in the tubes was determined in a gamma-counter. $^{125}$I counts were corrected for the contribution of the $^{131}$I signal to the total of registered counts in the $^{125}$I channel (15% of $^{131}$I counts as determined for a dilution series of $^{131}$I-DNA in PBS).

Two series of control experiments were performed. In the first set LS174T cells (50 µl) were incubated with $^{125}$I-labeled anti-CEA (25 µl, 1.0 µCi) during 30 minutes at 37° C., before the addition of $^{131}$I-Ran B-V (Scheme 7). RAN-incubations were carried out in duplicate according to the protocol described above for the anti-CEA-DNA conjugate. The second control series involved incubation of the microemboli (50 µl) in additional medium (50 µl) during 30 minutes at 37° C. (no antibody added), followed by incubation with $^{131}$I-RAN as above in duplicate.

Figure 3A:
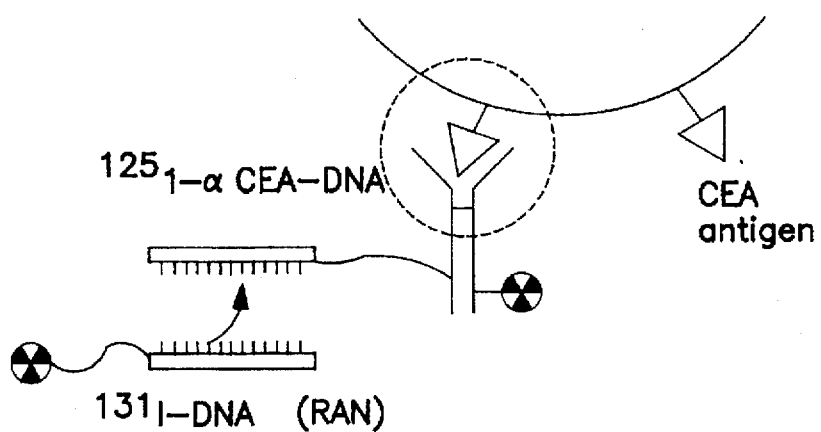
FIG. 3A shows a graphic representation of anti-CEA-DNA attaching to tumor cells followed by the attachment of a RAN.
Figure 3B:
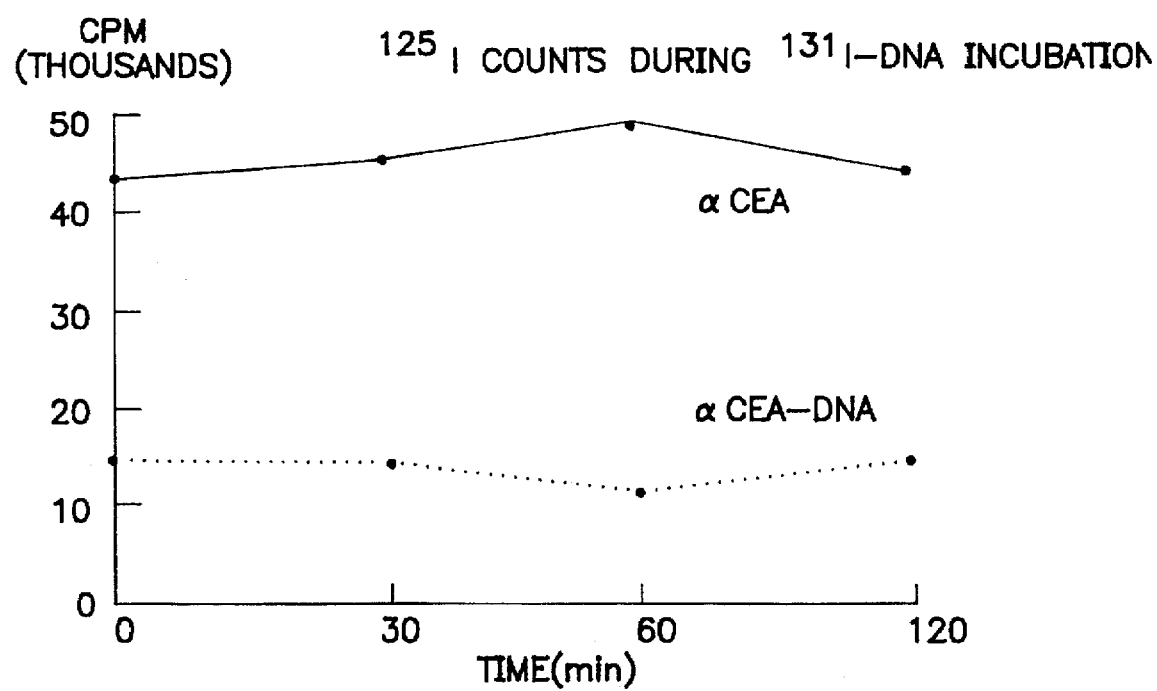

During performance of the second step, i.e. incubation with $^{131}$I-RAN (B-V), the amount of anti-CEA-DNA conjugate bound remains unchanged (FIG. 3B). Consequently, the amount of DNA available for hybridization with complementary RAN is constant as well.

Figure 4A:
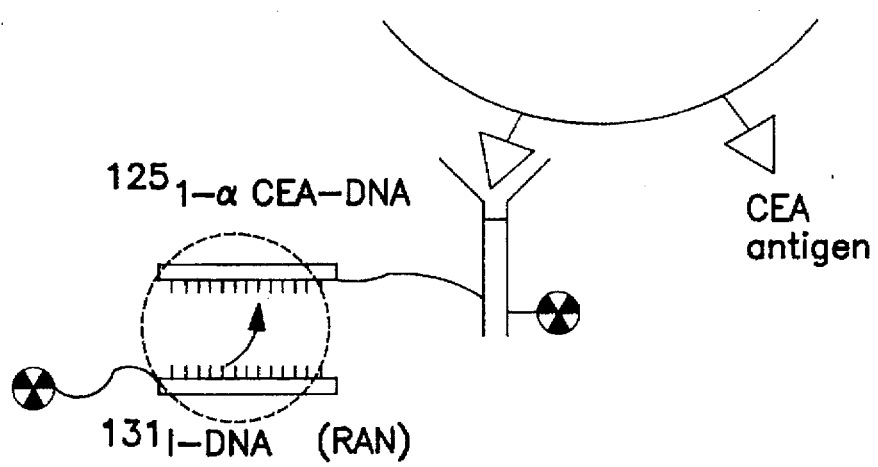
FIG. 4A shows a graphic representation of anti-CEA-DNA attaching to tumor cells followed by the attachment of a RAN.
Figure 4B:
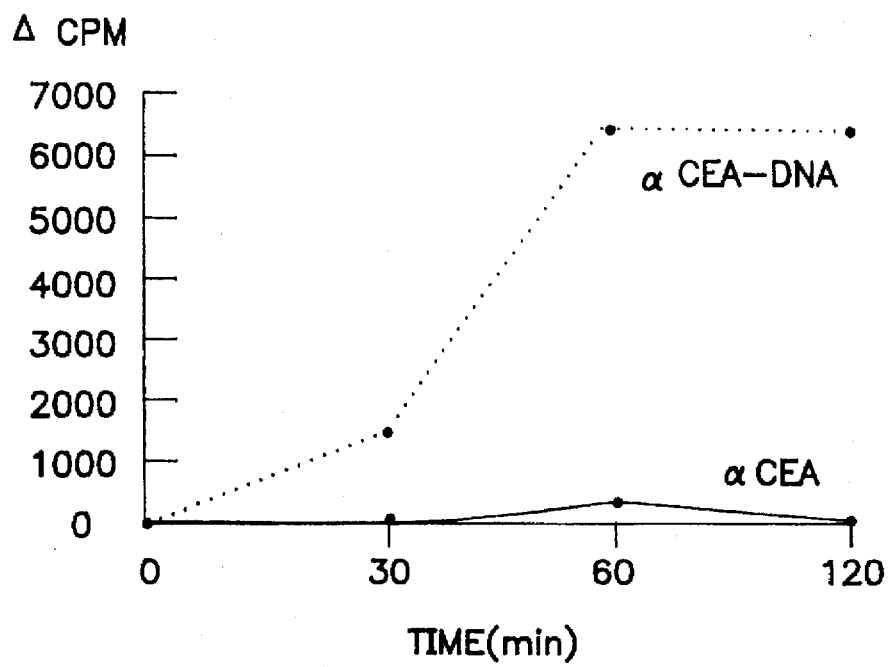
FIG. 4B is a graph showing that during incubation with the RAN the amount of anti-CEA-DNA conjugate bound remains unchanged.

Incubation of the microemboli with $^{131}$I-labeled RAN was performed at 37° C. for various time periods. The incubations were terminated by removal of the medium and several washings with fresh cold medium. Finally, the amount of $^{131}$I-radioactivity at the microemboli was determined (FIG. 4B). The microemboli pre-incubated with the anti-CEA-DNA conjugate revealed binding of significantly higher amounts of $^{131}$I-RAN. FIG. 4 shows the absolute $^{131}$I-counts corrected for the non-specific binding found in the control experiment. From these results it can be concluded that (part of) the RAN has hybridized specifically with the antibody-conjugated oligonucleotides. The hybridization turns out to be time-dependent, reaching saturation in approx. 1 hour. According to the amount of hybridized RAN related to the amount of anti-CEA-DNA conjugate bound to the cells, one can conclude that hybridization has taken place very efficiently.

The oligonucleotide C-II was incubated with a 30 molar excess of SPDP (S-pyridyl-dithiopropionate) in 0.05 mol/l sodium phosphate pH 8.5, containing 1 mmol/l EDTA. After 30 min. at ambient temperature, dithiothreitol was added to a final concentration of 10 mmol/1. Reduction was allowed for 20 min. at ambient temperature. The reaction mixture was then applied on a Q-SEPHAROSE column, 1.0×1.0 cm in size, equilibrated in the phosphate buffer mentioned above. The SH-containing DNA binds firmly to the column and is eluted at 0.6 mol/l NaCl in phosphate buffer. The SH-content of the oligonucleotide ranges between 0.9 and 1.1. as determined spectrophotometrically with DTNB.

The maleimide-substituted antibodies and the SH-oligonucleotide are mixed at a molar DNA-antibody ratio of 10. After an overnight incubation at ambient temperature, the reaction mixture is applied on a Q-SEPHAROSE column equilibrated in 0.05 mol/l sodium phosphate buffer pH 8.5, 1 mmol/l EDTA.

Section C

Oligonucleotides:

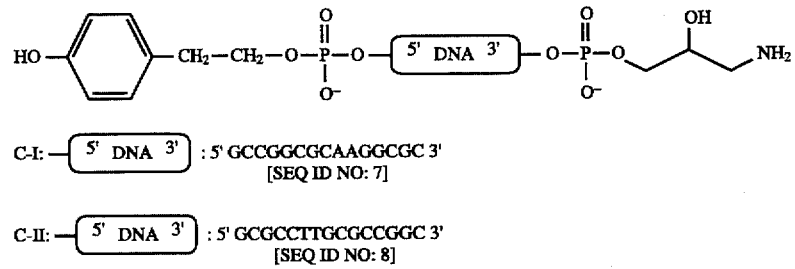

C-I: —[5' DNA 3'] : 5' GCCGGCGCAAGGCGC 3'
[SEQ ID NO: 7]

C-II: —[5' DNA 3'] : 5' GCGCCTTGCGCCGGC 3'
[SEQ ID NO: 8]

These fragments contain natural phosphodiester linkages. The 3'-end is protected against nuclease degradation by the introduction of a phosphopropylamino group. According to literature (Zendegui et al., Nucleic Acids Research, 20, 307) this moiety offers sufficient protection against exonucleases. Moreover, the terminal NH$_2$-group serves as a handle for the incorporation of various linkers in order to obtain oligonucleotides suitable for conjugation with monoclonal antibodies.

The oligonucleotides were prepared by automated synthesis on a CPG support (P.S. Nelson et al.: Nucleic Acids Research 17 (1989), 7187) with an trifluoroacetyl amino protecting group instead of the described Fmoc-group, using "standard" DNA-synthesizing conditions.

The p-hydroxyphenylethyl moiety was introduced in the last synthetic cycle using phosphoramidite B-III (Scheme 6). Removal from the solid support was achieved by treatment with aq. ammonia.

Example C-1

Preparation of antibody-oligonucleotide conjugates.

Antibody 16-88, a human IgM directed to a tumor-associated antigen (cytokeratin), and an irrelevant human IgM were reacted for 30 min with a 35 molar excess of GMBS 0.05 mol/l sodium phosphate buffer pH 7.5 containing 1 mmol/l EDTA. Excess reagent was removed by gel filtration on SEPHADEX G-25 (PD-10 column). The protein containing fractions were pooled and the maleimide content of the antibodies was determined spectrophotometrically using the cysteamine back titration procedure with DTNB (5,5'-dithio-bis-[2-nitrobenzoic acid]). Usually a substitution ratio ranging from 10–14 was found for both antibodies.

The bulk of the DNA-MoAb conjugates are eluted with 0.1 mol/l NaCl in phosphate buffer. Under the conditions applied, the DNA-antibody ratio was found to range from 4–6 as determined spectrophotometrically.

Example C-2

ELISA involving "DNA-DNA pretargeting"

For the ELISA-experiment the "RAN-sequence" C-I was labeled with biotin according to the following procedure. The complementary DNA strand (RAN) was incubated with a 40 molar excess of NHS-biotin in 0.05 mol/l sodium phosphate buffer pH 8.5 for 30 min. at ambient temperature. Excess reagent was removed by ion-exchange chromatography on Q-SEPHAROSE. The biotinylated RAN (BIO-RAN) was eluted at 0.6 mol/l NaCl in phosphate buffer.

Microtiter plates were coated with 10 μg/ml CTA*1 (the cognate antigen of MoAb 16-88) in PBS overnight at 4° C. The contents of the wells were discarded and the plates were washed twice with PBS-TWEEN. Excess protein binding sites were blocked by incubation with 50 g/l Skim milk (Blotto) for 2 h at ambient temperature. After discarding the blocking agent plates were washed with PBS-TWEEN and serial dilutions of 16-88-DNA, 16-88 and myeloma-DNA in PBS-buffer containing 10 g/l BSA were pipetted into the wells. Incubation was performed for 1 h at ambient temperature. Subsequently after discarding the contents and thorough washing with PBS-TWEEN one plate was incubated with goat-a-human IgM peroxidase conjugate in PBS-BSA for 1 h at ambient temperature. Another plate was incubated with 1 μg/ml Bio-RAN in PBS-DNA for 1 h and subsequently after washing with PBS-TWEEN. With streptavidin HRP. End point determination was carried out with a substrate solution containing H$_2$O$_2$ and TMB in acetate buffer pH 5.5. After washing the plates four times with PBS-TWEEN, the reaction was stopped by the addition of 2 mol/l $H_2SO_4$ and the absorbance was read at 450 nm in an Anthos reader.

Figure 5:
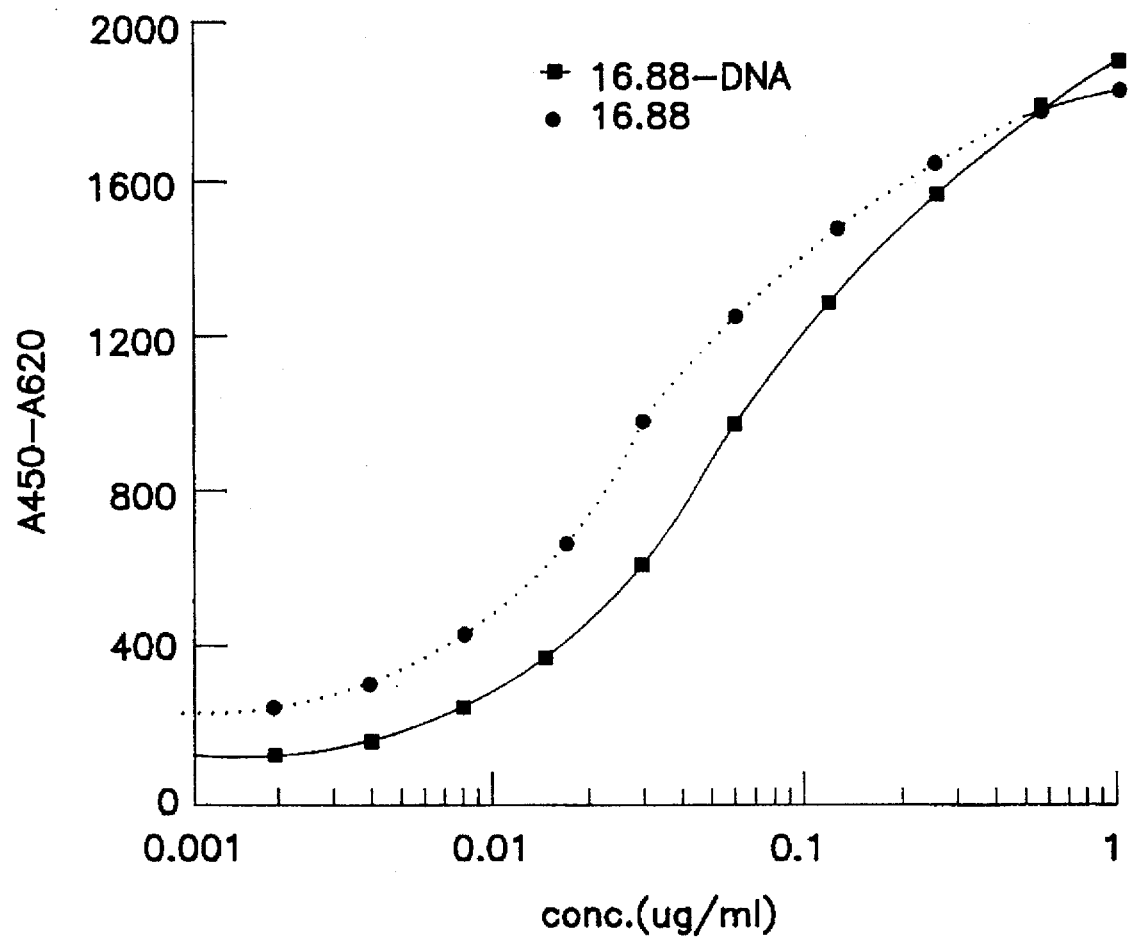
FIG. 5 is a graph showing the absorbance versus concentration of 16-88 alone or 16-88 conjugated to DNA.
Figure 6:
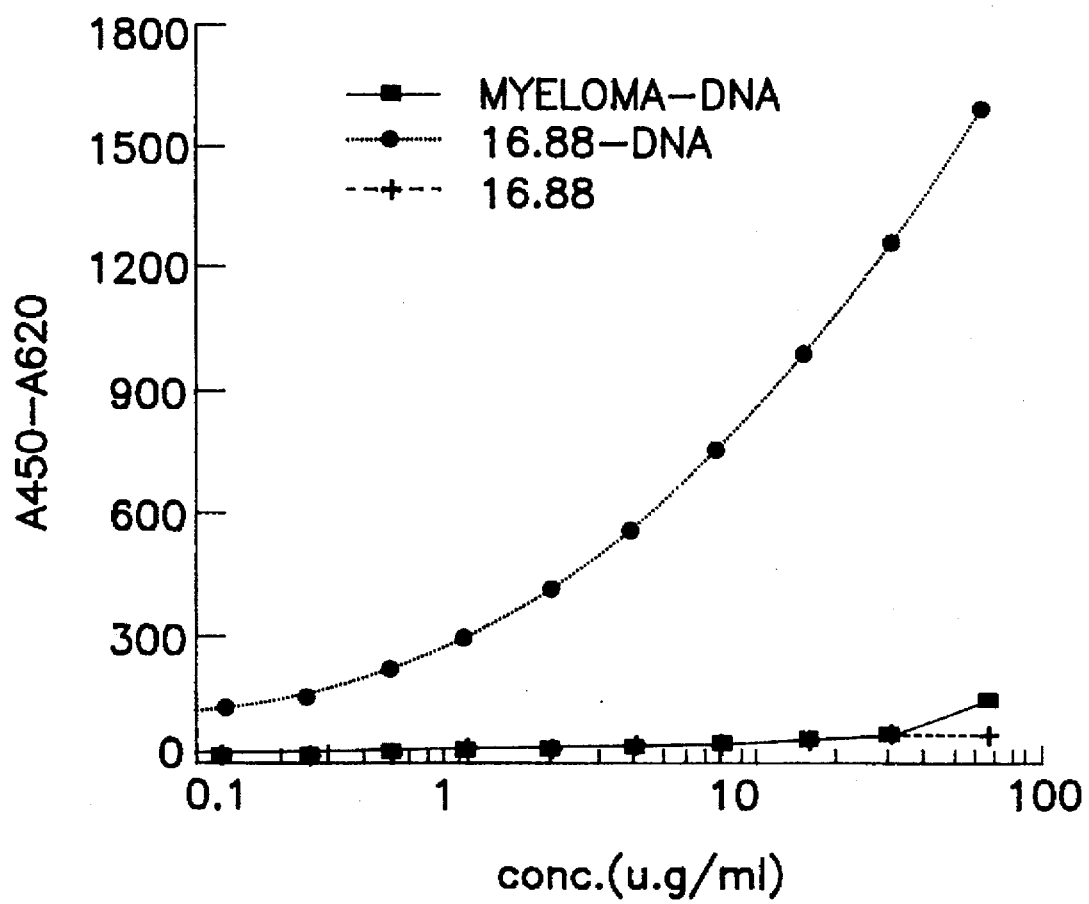
FIG. 6 is a graph showing the absorbance versus concentration of 16-88 alone, the 16-88 conjugated to DNA, and a myeloma-DNA conjugate.

The results are shown in FIGS. 5 and 6. From FIG. 5 it is concluded that there is still a substantial immunoreactivity after coupling the DNA to the antibody.

In FIG. 6 only the wells in which 16-88-DNA conjugate had been incubated gave a positive response with streptavidin HRP indicating that the BIORAN hybridized efficiently with the oligonucleotide present in the immune complex on the solid phase. The irrelevant immunoconjugate and the unmodified 16-88 showed the predicted negative reaction. The myeloma-DNA immunoconjugate should not react with the solid phase-bound antigen (irrelevant antibody), whereas 16-88 should bind to the plates but lacks the oligonucleotide. So, in both situations no reaction with the BIORAN is expected.

As is obvious, the ELISA as carried out according to the procedure outlined above mimicks the two-step targeting at the surface of a tumor cell bearing the tumor antigen.

We claim:

1. A kit for the targeted delivery of a therapeutically active radioisotope, comprising:

(a) at least one dosage unit containing a first composition comprising an oligonucleotide having 10–40 nucleotide bases, which is labeled with a therapeutically active radioisotope, wherein the oligonucleotide is chemically modified such that it will have increased resistance to nucleases but will allow for base pairing; and (b) at least one dosage unit containing a second composition comprising a conjugate of a targeting moiety and an oligonucleotide having 10–40 nucleotide bases, wherein the oligonucleotide is chemically modified such that it will have increased resistance to nucleases but will allow for base pairing;

wherein the modified oligonucleotide of the first composition is complementary to the modified oligonucleotide of the second composition.

2. The kit of claim 1, wherein the targeting moiety is an antibody or a fragment or a derivative thereof.

3. The kit of claim 1, wherein the labeled modified oligonucleotide of the first composition has the formula

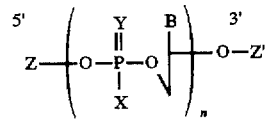

wherein n=10–40;

each B is independently selected from the group consisting of a nucleoside base (C, G, A, T, U) and analogous bases;

each X is independently selected from the group consisting of O⁻, S⁻, N-dialkyl, O-alkyl and alkyl;

each Y is independently selected from the group consisting of O and S;

Z and Z' are independently selected from the group consisting of H, alkyl, aralkyl, acyl, nucleoside and a chemical group which contains a therapeutically active radioisotope, provided that Z' is not H or nucleoside when X is O⁻ or Y is O, and that one but not both of Z and Z' is the chemical group containing the isotope;

and wherein the modified oligonucleotide of the second composition has the formula

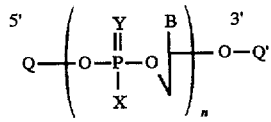

wherein n=10–40;

each B is independently selected from the group consisting of a nucleoside base (C, G, A, T, U) and analogous bases;

each X is independently selected from the group consisting of O⁻, S⁻, N-dialkyl, O-alkyl and alkyl;

each Y is independently selected from the group consisting of O and S;

one of Q and Q' is a chemical group which is suitable for conjugation with a targeting moiety, and the other is selected from the group consisting of H, alkyl, aralkyl, acyl and nucleoside;

wherein the modified oligonucleotide of the second composition is optionally labeled with an isotope suitable for imaging;

and wherein the modified oligonucleotide of the first composition is complementary to the modified oligonucleotide of the second composition.

4. The kit of claim 1, wherein the modified oligonucleotide of the first composition is an oligonucleotide having the formula

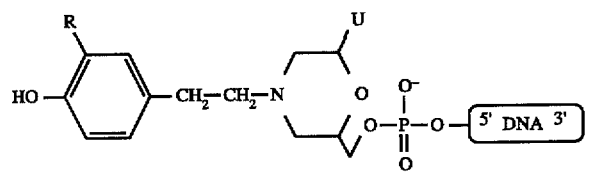

[SEQ ID NO: 3]

wherein R=$^{125}$I;

and the modified oligonucleotide of the second composition is an oligonucleotide having the formula

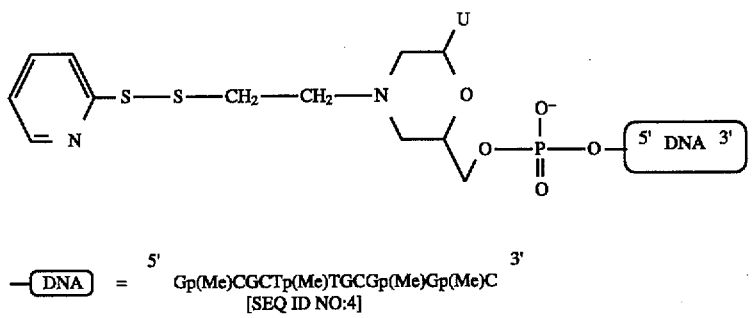

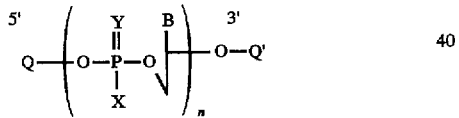 = 5' Gp(Me)CGCTp(Me)TGCGp(Me)Gp(Me)C 3'
[SEQ ID NO:4]

which is conjugated to antibody 16-88, deposited at the ATCC under Accession No. HB 8495.

5. A method of treating tumors, comprising:

(a) administering to a patient a composition comprising a conjugate of an antibody, or a fragment or a derivative thereof, and an oligonucleotide in a therapeutically effective dosage, wherein said oligonucleotide has 10–40 nucleotide bases and is chemically modified such that it will have increased resistance to nucleases but will allow for base pairing; and (b) subsequent to step (a), administering a therapeutically effective dosage of a composition comprising an oligonucleotide, labeled with a therapeutically active radioisotope, which is complementary to the first administered oligonucleotide, wherein said oligonucleotide has 10–40 nucleotide bases and is chemically modified such that it will have increased resistance to nucleases but will allow for base pairing.

6. The method of claim 5, wherein the modified oligonucleotide of said conjugate of step (a) has the formula $$5'\ Q\!-\!\!\left(\!O\!-\!\!\overset{\overset{\displaystyle Y}{\|}}{\underset{\underset{\displaystyle X}{|}}{P}}\!-\!O\!-\!\!\left[\!\!\begin{array}{c}B\\ \end{array}\!\!\right]\!\right)_{\!n}\!\!-\!O\!-\!Q'\ 3'$$

wherein n=10–40;

each B is independently selected from the group consisting of a nucleoside base (C, G, A, T, U) and analogous bases;

each X is independently selected from the group consisting of O⁻, S⁻, N-dialkyl, O-alkyl and alkyl;

each Y is independently selected from the group consisting of O and S;

one of Q and Q' is a chemical group which is suitable for conjugation with a targeting moiety, and the other is selected from the group consisting of H, alkyl, aralkyl, acyl and nucleoside;

wherein the modified oligonucleotide is optionally labeled with an isotope suitable for imaging;

and wherein the modified oligonucleotide labeled with a therapeutically active isotope of step (b) has the formula $$5'\ Z\!-\!\!\left(\!O\!-\!\!\overset{\overset{\displaystyle Y}{\|}}{\underset{\underset{\displaystyle X}{|}}{P}}\!-\!O\!-\!\!\left[\!\!\begin{array}{c}B\\ \end{array}\!\!\right]\!\right)_{\!n}\!\!-\!O\!-\!Z'\ 3'$$

wherein n=10–40;

each B is independently selected from the group consisting of a nucleoside base (C, G, A, T, U) and analogous bases;

each X is independently selected from the group consisting of O⁻, S⁻, N-dialkyl, O-alkyl and alkyl;

each Y is independently selected from the group consisting of O and S;

z and Z' are independently selected from the group consisting of H, alkyl, aralkyl, acyl, nucleoside and a chemical group which contains a therapeutically active radioisotope, provided that Z' is not H or nucleoside when X is O⁻ or Y is O, and that one but not both of Z and Z' is the chemical group containing the isotope;

and wherein the modified oligonucleotides are complementary.

7. A method for treating tumors, comprising sequentially administering to a patient a composition comprising a conjugate of antibody 16-88, which is deposited at the ATCC under Accession No. HB 8495, and an oligonucleotide having the formula

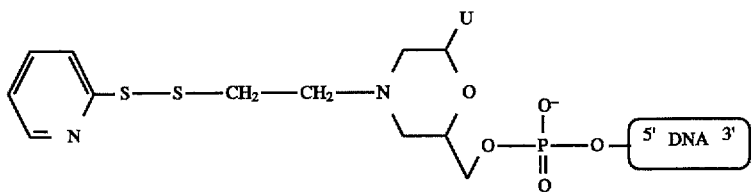
in a therapeutically effective dosage, followed by administering a therapeutically effective dosage of a composition comprising an oligonucleotide having the formula
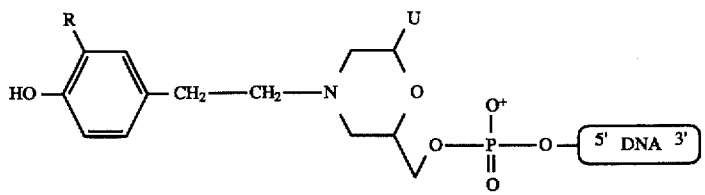
wherein R=$^{125}$I;
and wherein said oligonucleotides contain regions that are complementary to each other.
* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Synthetic Oligonucleotides"

( i i i ) HYPOTHETICAL: NO ( i x ) FEATURE:
        ( A ) NAME/KEY: misc_feature
        ( B ) LOCATION: 1..2
        ( D ) OTHER INFORMATION: /note= "The bond between these two bases is 5'-5'"

( i x ) FEATURE:
        ( A ) NAME/KEY: misc_feature
        ( B ) LOCATION: 2
        ( D ) OTHER INFORMATION: /note= "This base is Gp(Me)"

( i x ) FEATURE:
        ( A ) NAME/KEY: misc_feature
        ( B ) LOCATION: 14
        ( D ) OTHER INFORMATION: /note= "This base is Gp(Me)"

( x i ) SEQUENCE DESCRIPTION: SEQ ID NO:1:

UGCCGGCGCA AGCGC                  15

( 2 ) INFORMATION FOR SEQ ID NO:2:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Synthetic oligonucleotide"

( i x ) FEATURE:
        ( A ) NAME/KEY: misc_feature
        ( B ) LOCATION: 1..2
        ( D ) OTHER INFORMATION: /note= "Bond between u and g is 5'-5'"

( i x ) FEATURE:
        ( A ) NAME/KEY: misc_feature
        ( B ) LOCATION: 2
        ( D ) OTHER INFORMATION: /note= "This base is Gp(Me)"

( i x ) FEATURE:

(A) NAME/KEY: misc_feature
                (B) LOCATION: 6
                (D) OTHER INFORMATION: /note= "This base is Tp(Me)"

(ix) FEATURE:
                (A) NAME/KEY: misc_feature
                (B) LOCATION: 10
                (D) OTHER INFORMATION: /note= "This base is Gp(Me)"

(ix) FEATURE:
                (A) NAME/KEY: misc_feature
                (B) LOCATION: 13..14
                (D) OTHER INFORMATION: /note= "These two bases are Gp(Me)"

(xi) SEQUENCE DESCRIPTION: SEQ ID NO:2:

UGCGCTTGCG CCGGC                                                                                            15

(2) INFORMATION FOR SEQ ID NO:3:

(i) SEQUENCE CHARACTERISTICS:
                (A) LENGTH: 14 base pairs
                (B) TYPE: nucleic acid
                (C) STRANDEDNESS: single
                (D) TOPOLOGY: linear (ii) MOLECULE TYPE: other nucleic acid
                (A) DESCRIPTION: /desc = "synthetic oligonucleotide"

(ix) FEATURE:
                (A) NAME/KEY: misc_feature
                (B) LOCATION: 1
                (D) OTHER INFORMATION: /note= "This base is Gp(Me)"

(ix) FEATURE:
                (A) NAME/KEY: misc_feature
                (B) LOCATION: 13
                (D) OTHER INFORMATION: /note= "This base is Gp(Me)"

(xi) SEQUENCE DESCRIPTION: SEQ ID NO:3:

GCCGGCGCAA GCGC                                                                                             14

(2) INFORMATION FOR SEQ ID NO:4:

(i) SEQUENCE CHARACTERISTICS:
                (A) LENGTH: 14 base pairs
                (B) TYPE: nucleic acid
                (C) STRANDEDNESS: single
                (D) TOPOLOGY: linear (ii) MOLECULE TYPE: other nucleic acid
                (A) DESCRIPTION: /desc = "synthetic olionucleotide"

(ix) FEATURE:
                (A) NAME/KEY: misc_feature
                (B) LOCATION: 1
                (D) OTHER INFORMATION: /note= "This base is Gp(Me)"

(ix) FEATURE:
                (A) NAME/KEY: misc_feature
                (B) LOCATION: 5
                (D) OTHER INFORMATION: /note= "This base is Tp(Me)"

(ix) FEATURE:
                (A) NAME/KEY: misc_feature
                (B) LOCATION: 9
                (D) OTHER INFORMATION: /note= "This base is Gp(Me)"

(ix) FEATURE:
                (A) NAME/KEY: misc_feature
                (B) LOCATION: 12..13
                (D) OTHER INFORMATION: /note= "These two bases are Gp(Me)"

(xi) SEQUENCE DESCRIPTION: SEQ ID NO:4:

GCGCTTGCGC CGGC                                                                                             14

( 2 ) INFORMATION FOR SEQ ID NO:5:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "synthetic oligonucleotide"

( i x ) FEATURE:
        ( A ) NAME/KEY: misc_feature
        ( B ) LOCATION: 1
        ( D ) OTHER INFORMATION: /note= "This base is Gp(Me)"

( i x ) FEATURE:
        ( A ) NAME/KEY: misc_feature
        ( B ) LOCATION: 14
        ( D ) OTHER INFORMATION: /note= "This base is Gp(Me)"

( x i ) SEQUENCE DESCRIPTION: SEQ ID NO:5:

GCCGGCGCAA GGCGC 15

( 2 ) INFORMATION FOR SEQ ID NO:6:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "synthetic oligonucleotide"

( i x ) FEATURE:
        ( A ) NAME/KEY: misc_feature
        ( B ) LOCATION: 1
        ( D ) OTHER INFORMATION: /note= "This base is Gp(Me)"

( i x ) FEATURE:
        ( A ) NAME/KEY: misc_feature
        ( B ) LOCATION: 6
        ( D ) OTHER INFORMATION: /note= "This base is Tp(Me)"

( i x ) FEATURE:
        ( A ) NAME/KEY: misc_feature
        ( B ) LOCATION: 10
        ( D ) OTHER INFORMATION: /note= "This base is Gp(Me)"

( i x ) FEATURE:
        ( A ) NAME/KEY: misc_feature
        ( B ) LOCATION: 13..14
        ( D ) OTHER INFORMATION: /note= "These two bases are Gp(Me)"

( x i ) SEQUENCE DESCRIPTION: SEQ ID NO:6:

GCGCCTTGCG CCGGC 15

( 2 ) INFORMATION FOR SEQ ID NO:7:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "synthetic oligonucleotide"

( x i ) SEQUENCE DESCRIPTION: SEQ ID NO:7:

GCCGGCGCAA GGCGC 15

( 2 ) INFORMATION FOR SEQ ID NO:8:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( i i ) MOLECULE TYPE: other nucleic acid
  ( A ) DESCRIPTION: /desc = "synthetic oligonucleotide"

( x i ) SEQUENCE DESCRIPTION: SEQ ID NO:8:

GCGCCTTGCG CCGGC    15